(12) United States Patent
Vladar et al.

(10) Patent No.: US 11,352,619 B2
(45) Date of Patent: Jun. 7, 2022

(54) METHOD FOR SYNTHESIS OF POLYNUCLEOTIDES USING A DIVERSE LIBRARY OF OLIGONUCLEOTIDES

(71) Applicant: Ribbon Biolabs GmbH, Vienna (AT)

(72) Inventors: Harold Paul Vladar, Vienna (AT); Rodrigo Aparecido Fernandes Redondo, London (GB)

(73) Assignee: RIBBON BIOLABS GMBH, Vienna (AT)

( * ) Notice: Subject to any disclaimer, the term of this patent is extended or adjusted under 35 U.S.C. 154(b) by 0 days.

(21) Appl. No.: 16/753,317

(22) PCT Filed: Oct. 15, 2018

(86) PCT No.: PCT/EP2018/078016
§ 371 (c)(1),
(2) Date: Apr. 2, 2020

(87) PCT Pub. No.: WO2019/073072
PCT Pub. Date: Apr. 18, 2019

(65) Prior Publication Data
US 2020/0283756 A1 Sep. 10, 2020

(30) Foreign Application Priority Data
Oct. 13, 2017 (EP) .................................... 17196317

(51) Int. Cl.
*C12N 15/10* (2006.01)
*C12N 15/66* (2006.01)

(52) U.S. Cl.
CPC ..... *C12N 15/1031* (2013.01); *C12N 15/1058* (2013.01)

(58) Field of Classification Search
CPC ............ C12N 15/1031; C12N 15/1058; C12N 15/1027; C12N 15/66; C12N 15/10
See application file for complete search history.

(56) References Cited

U.S. PATENT DOCUMENTS

| 2007/0122817 A1* | 5/2007 | Church ................ C12Q 1/6806 435/6.16 |
|---|---|---|
| 2011/0172127 A1 | 7/2011 | Jacobson et al. |
| 2016/0215316 A1 | 7/2016 | Pedersen et al. |

FOREIGN PATENT DOCUMENTS

| WO | 02081490 A3 | 10/2002 |
|---|---|---|
| WO | 2004033619 A3 | 4/2004 |
| WO | 2009138954 A2 | 11/2009 |

OTHER PUBLICATIONS

Blackburn, in Nucleic Acids in Chemistry and Biology, 1996 (Year: 1996).*

(Continued)

*Primary Examiner* — Jeremy C Flinders
*Assistant Examiner* — Taryn Kimberly Wood
(74) *Attorney, Agent, or Firm* — Loza & Loza, LLP; Michael F. Fedrick

(57) ABSTRACT

A method for synthesizing a target double stranded (ds) polynucleotide by
providing an oligonucleotide library within an array device that has a diversity of oligonucleotide library members, each of which has a different nucleotide sequence and is contained in a separate library containment in an aqueous solution. The library includes single stranded oligonucleotides and double stranded oligonucleotides with at least one overhang and covers at least 10,000 pairs of matching oligonucleotides.
In a first step, transferring at least a first pair of matching oligonucleotides transferred from the library into a first reaction containment using a liquid handler and the matching oligonucleotides are assembled, thereby obtaining a first reaction product comprising at least one overhang. Further reaction products are then likewise obtained
and are assembled in a predetermined workflow using an algorithm, thereby producing said target ds polynucle- (Continued)

Figures 4, 5:
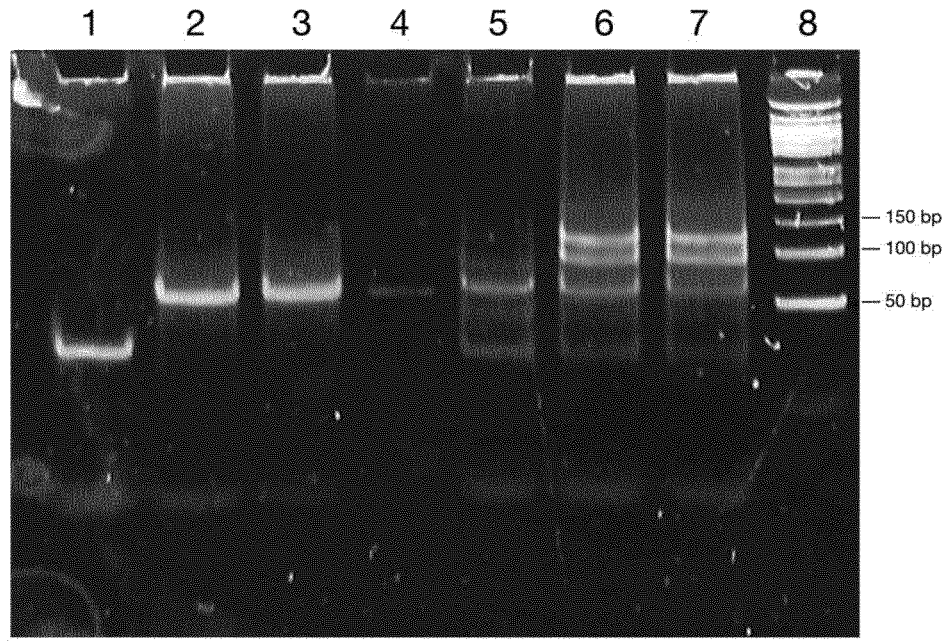

otide with an overhang, optionally followed by a finalization step to prepare blunt ends.

21 Claims, 9 Drawing Sheets

Specification includes a Sequence Listing.

(56) References Cited

OTHER PUBLICATIONS

Anderson et al. "Sequence and organization of the human mitochondrial genome." Nature vol. 290 pp. 457-465 (Apr. 9, 1981).
Beaucage et al. "Deoxynucleoside phosphoramidites—a new class of key intermediates for deoxypolynucleotide synthesis." Tetrahedron Letters, vol. 22:20, pp. 1859-1862 (1981).
Bently et al. "Accurate whole human genome sequencing using reversible terminator chemistry." Nature:456 (7218): 53-59 (Nov. 6, 2008).
Bonde et al. "Direct mutagenesis of thousands of genomic targets using microarray-derived oligonucleotides." ACS Synth. Biol. 2015, 4:17-22 (May 23, 2014).
Brutlag et al. "Improved sensitivity of biological sequence database searches." Bioinformatics, Vo. 6, Issue 3, pp. 237-245 (Jul. 1990).
Chari et al. "Beyond editing to writing large genomes." Nat Rev Genet. 18(12): 749-760 (Dec. 2017).
Engler et al. "A one pot, one step, precision cloning method with high throughput capability." PLoS One vol. 3 | Issue 11 | e3647 (Nov. 2008).
Farzadfard et al. "Genomically encoded analog memory with precise in vivo dna writing in living cell populations." Science 346(6211) (Nov. 14, 2014).
Gao et al. "A flexible light-directed DNA chip synthesis gated by deprotection using solution photogenerated acids." Nucleic Acids Research, vol. 29, Issue 22, pp. 4744-4750 (Nov. 15, 2001).
Gibson et al. "Enzymatic assembly of DNA molecules up to several hundred kilobases." Nature Methods vol. 6(5): 343-345 (5 pages) (2009).
Horspool et al. "Efficient assembly of very short oligonucleotides using T4 DNA Ligase." BMC Research Notes 3:291 (2010).
Kai et al. "A novel microfluidic microplate as the next generation assay platform for enzyme linked immunoassays (ELISA)." Lab Chip, 12:4257-4262 (2012).
Lehman et al. "The deoxyribonucleases of *Escherichia coli*." J. Biol. Chem. vol. 239(8)2628-2636 (Jan. 1964).
Leproust et al. "Synthesis of high-quality libraries of long (150mer) oligonucleotides by a novel depurination controlled process." Nucleic Acids Research vol. 38(8): 2522-2540 (Mar. 22, 2010).
Nuener et al. "Codon-based mutagenesis using dimer-phosphoramidites." Nucleic Acids Research, vol. 26(5):1223-1227 (1998).
Smith et al. "Generating a synthetic genome by whole genome assembly: φX174 bacteriophage from synthetic oligonucleotides." PNAS, 100(26):15440-15445 (Dec. 23, 2003).
Sondek et al. "A general strategy for random insertion and substitution mutagenesis: substoichiometric coupling of trinucleotide phosphoramidites." PNAS, 89:3581-3585 (Apr. 15, 1992).
Stemmer et al. "Single-step assembly of a gene and entire plasmid from large numbers of oligodeoxyribonucleotides." Gene, 164:49-53 (1995).
European Patent Appln. No. 17196317.6, Extended EP Search Report (dated Jan. 3, 2018).
Kemp, "Capillary electrophoresis: a versatile family of analytical techniques." Biotechnol. Appl. Biochem, 27:9-17 (1998).
PCT Appln. No. PCT/EP2018/078016, Int'l Preliminary Report on Patentability & Written Opinion (dated Apr. 14, 2020).
International Patent Application No. PCT/EP2018/078016, International Search Report, 4 pages (dated Nov. 28, 2018).
International Patent Application No. PCT/EP2018/078016, Written Opinion, 6 pages (dated Nov. 28, 2018).

* cited by examiner

> DISCOVER sequence
SEQ ID NO: 1
TTTCTTCTTTCGAGTTTCTATATCCGTCGCTGGTCTGAACGGAAAAATCATCGCACAATCTATGCC
TACCGTTGGCTGCTCATGCGTCCTTCCGACAATCCCATGTTCGTCTCGCATCCGTTTCCTGC

B)

> D+
SEQ ID NO: 2
TTTCTTCTTTCGAGTT
> D-
SEQ ID NO: 3
TAGAAACTCGAAAGAA

> I+
SEQ ID NO: 4
TCTATATCCGTCGCTG
> I-
SEQ ID NO: 5
AGACCAGCGACGGATA

> S+
SEQ ID NO: 6
GTCTGAACGGAAAAAT
> S-
SEQ ID NO: 7
GATGATTTTTCCGTTC

> C+
SEQ ID NO: 8
CATCGCACAATCTATG
> C-
SEQ ID NO: 9
TAGGCATAGATTGTGC

> O+
SEQ ID NO: 10
CCTACCGTTGGCTGCT
> O-
SEQ ID NO: 11
CATGAGCAGCCAACGG

> V+
SEQ ID NO: 12
CATGCGTCCTTCCGAC
> V-
SEQ ID NO: 13
GATTGTCGGAAGGACG

> E+
SEQ ID NO: 14
AATCCCATGTTCGTCT
> E-
SEQ ID NO: 15
TGCGAGACGAACATGG

> R+
SEQ ID NO: 16
CGCATCCGTTTCCTGC
> R-
SEQ ID NO: 17
GCGTGCAGGAAACGGA

C)

> D+
SEQ ID NO: 2
TTTCTTCTTTCGAGTT----
> D-
SEQ ID NO: 25
----AAGAAAGCTCAAAGAT

FIGURE 3
A)
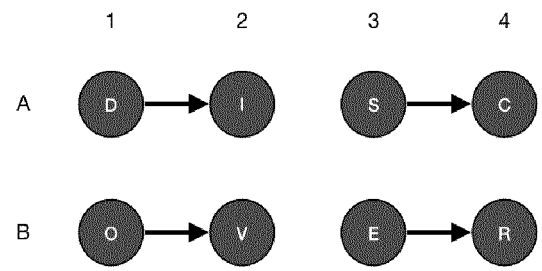
B)
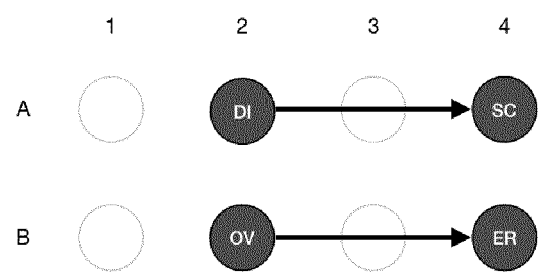
C)
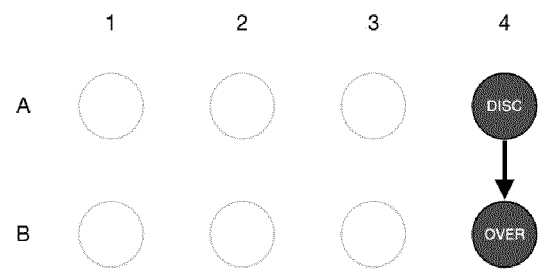

A)

CCTACCGTTGGCTGCTAATCCGTCCTTCCGACAATC...

....GGCAACCGACGATTAGGCAGGAAGGCTGTTAG...

B)

CCTACCGTTGGCTGCTCATGCGTCCTTCCGACAATC...

....GGCAACCGACGAGTACGCAGGAAGGCTGTTAG...

C)

GTTGGCTGCTAATCCGTCCTTCCG

CGGAAGGACGCATGAGCAGCCAAC

FIGURE 6

|   | A | B | C | D | E | F | G | H |
|---|---|---|---|---|---|---|---|---|
| 1 | A1+<br>A1- | B1+<br>B1- | C1+<br>C1- | D1+<br>D1- | E1+<br>E1- | F1+<br>F1- | G1+<br>G1- | H1+<br>H1- |
| 2 | A2+<br>A2- | B2+<br>B2- | C2+<br>C2- | D2+<br>D2- | X | X | X | H2+<br>H2- |
| 3 | A3+<br>A3- | B3+<br>B3- | C3+<br>C3- | D3+<br>D3- | X | X | X | H3+<br>H3- |
| 4 | A4+<br>A4- | B4+<br>B4- | C4+<br>C4- | D4+<br>D4- | X | X | X | H4+<br>H4- |
| 5 | A5+<br>A5- | B5+<br>B5- | C5+<br>C5- | D5+<br>D5- | X | X | X | H5+<br>H5- |
| 6 | A6+<br>A6- | B6+<br>B6- | C6+<br>C6- | D6+<br>D6- | X | X | X | H6+<br>H6- |
| 7 | A7+<br>A7- | B7+<br>B7- | C7+<br>C7- | D7+<br>D7- | X | X | X | H7+<br>H7- |
| 8 | X | X | X | X | X | X | X | X |
| 9 | X | X | X | X | X | X | X | X |
| 10 | X | X | X | X | X | X | X | X |
| 11 | X | X | X | X | X | X | X | X |
| 12 | X | X | X | X | X | X | X | X |

FIGURE 7

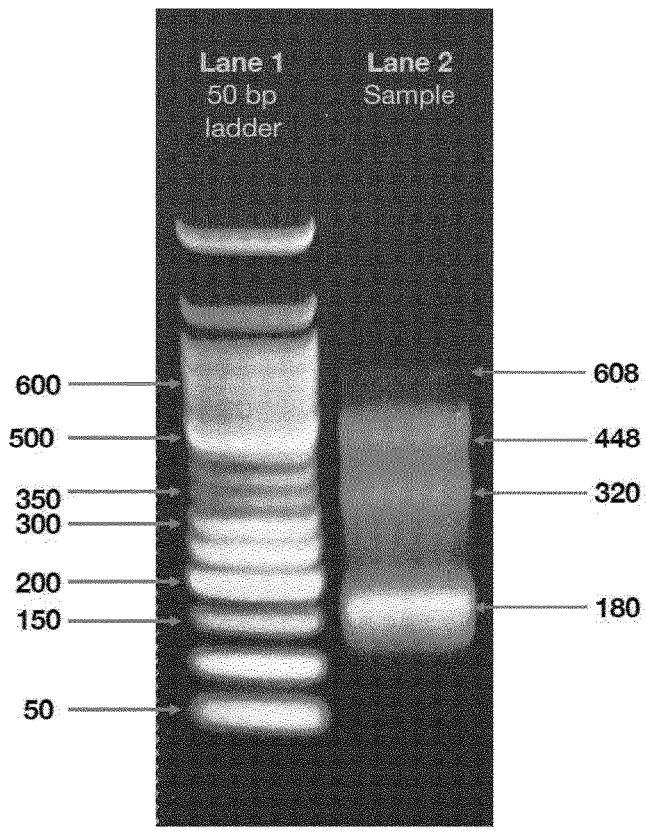

FIGURE 8

> Ribbon_test_608 (SEQ ID NO:26)

TTTCTTCTTTCGAGTTTCTATATCCGTCGCTGGTCTGAACGGAAAAATCATCGCACAATCTATGCCTAC
CGTTGGCTGCTCATGCGTCCTTCCGACAATCCCATGTTCGTCTCGCATCCGTTTCCTGCACGCACCCCC
CCCTGTACTTTGGAAAGCGGCCATCTTAACACTCTCCCAACTTTTTAAATGCGTCGAAGCCCTGGGCAT
CTGGTTTCCACTAGCCTAGTCGGGTGTTGGATACGCCGAGAGTTATGGTGTAGCTGTGTGCGCGAACCG
ACGGGTGGAAATTGCTGACCGATTTTCAAATAGTTCTCAGGAAGCCGATGGCAGTTACGGCTTGCGACT
CGGGGCACCGTGAGCCTCTTCTCCCTCTAGAAGTCGAAGCAAGGGACACTATCCTAAATGCCATGGACT
AGCGCGCGCGAAATCGATGCACTCCTTATTAATGTGATCTGCGCAAGTTGTTCAGCCATCGGTCATTTT
GCGTTGATATTCGGTTCTTTGATTTGCGTGCCATGCTTATAACAGGACACTTATTGTGCCCCAGCTCTT
CTCATGCAAGTGCGGTTTTCTCTAGCTACTGTGGTGTGCGCTCATCAATACTCCAG

FIGURE 8 continued

> A1+ (SEQ ID NO:27)
TTTCTTCTTTCGAGTT
> A1- (SEQ ID NO:28)
TAGAAACTCGAAAGAA
> B1+ (SEQ ID NO:29)
TCTATATCCGTCGCTG
> B1- (SEQ ID NO:30)
AGACCAGCGACGGATA
> C1+ (SEQ ID NO:31)
GTCTGAACGGAAAAAT
> C1- (SEQ ID NO:32)
GATGATTTTTCCGTTC
> D1+ (SEQ ID NO:33)
CATCGCACAATCTATG
> D1- (SEQ ID NO:34)
TAGGCATAGATTGTGC
> E1+ (SEQ ID NO:35)
CCTACCGTTGGCTGCT
> E1- (SEQ ID NO:36)
CATGAGCAGCCAACGG
> F1+ (SEQ ID NO:37)
CATGCGTCCTTCCGAC
> F1- (SEQ ID NO:38)
GATTGTCGGAAGGACG
> G1+ (SEQ ID NO:39)
AATCCCATGTTCGTCT
> G1- (SEQ ID NO:40)
TGCGAGACGAACATGG
> H1+ (SEQ ID NO:41)
CGCATCCGTTTCCTGC
> H1- (SEQ ID NO:42)
GCGTGCAGGAAACGGA
> A2+ (SEQ ID NO:43)
ACGCACCCCCCCCTGT

> A2- (SEQ ID NO:44)
AAGTACAGGGGGGGGT
> B2+ (SEQ ID NO:45)
ACTTTGGAAAGCGGCC
> B2- (SEQ ID NO:46)
AGATGGCCGCTTTCCA
> C2+ (SEQ ID NO:47)
ATCTTAACACTCTCCC
> C2- (SEQ ID NO:48)
AGTTGGGAGAGTGTTA
> D2+ (SEQ ID NO:49)
AACTTTTTAAATGCGT
> D2- (SEQ ID NO:50)
TTCGACGCATTTAAAA
> H2+ (SEQ ID NO:51)
CGAAGCCCTGGGCATC
> H2- (SEQ ID NO:52)
ACCAGATGCCCAGGGC
> A3+ (SEQ ID NO:53)
TGGTTTCCACTAGCCT
> A3- (SEQ ID NO:54)
GACTAGGCTAGTGGAA
> B3+ (SEQ ID NO:55)
AGTCGGGTGTTGGATA
> B3- (SEQ ID NO:56)
GGCGTATCCAACACCC
> C3+ (SEQ ID NO:57)
CGCCGAGAGTTATGGT
> C3- (SEQ ID NO:58)
CTACACCATAACTCTC
> D3+ (SEQ ID NO:59)
GTAGCTGTGTGCGCGA
> D3- (SEQ ID NO:60)
CGGTTCGCGCACACAG

FIGURE 8 continued

> H3+ (SEQ ID NO:61)
ACCGACGGGTGGAAAT
> H3- (SEQ ID NO:62)
AGCAATTTCCACCCGT
> A4+ (SEQ ID NO:63)
TGCTGACCGATTTTCA
> A4- (SEQ ID NO:64)
TATTTGAAAATCGGTC
> B4+ (SEQ ID NO:65)
AATAGTTCTCAGGAAG
> B4- (SEQ ID NO:66)
TCGGCTTCCTGAGAAC
> C4+ (SEQ ID NO:67)
CCGATGGCAGTTACGG
> C4- (SEQ ID NO:68)
CAAGCCGTAACTGCCA
> D4+ (SEQ ID NO:69)
CTTGCGACTCGGGGCA
> D4- (SEQ ID NO:70)
ACGGTGCCCCGAGTCG
> H4+ (SEQ ID NO:71)
CCGTGAGCCTCTTCTC
> H4- (SEQ ID NO:72)
GAGGGAGAAGAGGCTC
> A5+ (SEQ ID NO:73)
CCTCTAGAAGTCGAAG
> A5- (SEQ ID NO:74)
CTTGCTTCGACTTCTA
> B5+ (SEQ ID NO:75)
CAAGGGACACTATCCT
> B5- (SEQ ID NO:76)
ATTTAGGATAGTGTCC
> C5+ (SEQ ID NO:77)
AAATGCCATGGACTAG
> C5- (SEQ ID NO:78)
CGCGCTAGTCCATGGC

> D5+ (SEQ ID NO:79)
CGCGCGCGAAATCGAT
> D5- (SEQ ID NO:80)
GTGCATCGATTTCGCG
> H5+ (SEQ ID NO:81)
GCACTCCTTATTAATG
> H5- (SEQ ID NO:82)
ATCACATTAATAAGGA
> A6+ (SEQ ID NO:83)
TGATCTGCGCAAGTTG
> A6- (SEQ ID NO:84)
TGAACAACTTGCGCAG
> B6+ (SEQ ID NO:85)
TTCAGCCATCGGTCAT
> B6- (SEQ ID NO:86)
CAAAATGACCGATGGC
> C6+ (SEQ ID NO:87)
TTTGCGTTGATATTCG
> C6- (SEQ ID NO:88)
GAACCGAATATCAACG
> D6+ (SEQ ID NO:89)
GTTCTTTGATTTGCGT
> D6- (SEQ ID NO:90)
TGGCACGCAAATCAAA
> H6+ (SEQ ID NO:91)
GCCATGCTTATAACAG
> H6- (SEQ ID NO:92)
TGTCCTGTTATAAGCA
> A7+ (SEQ ID NO:93)
GACACTTATTGTGCCC
> A7- (SEQ ID NO:94)
GCTGGGGCACAATAAG
> B7+ (SEQ ID NO:95)
CAGCTCTTCTCATGCA
> B7- (SEQ ID NO:96)
CACTTGCATGAGAAGA

FIGURE 8 continued

> C7+ (SEQ ID NO:97)
AGTGCGGTTTTCTCTA
> C7- (SEQ ID NO:98)
TAGCTAGAGAAAACCG
> D7+ (SEQ ID NO:99)
GCTACTGTGGTGTGCG

> D7- (SEQ ID NO:100)
TGAGCGCACACCACAG
> H7+ (SEQ ID NO:101)
CTCATCAATACTCCAG
> H7- (SEQ ID NO:102)
TTATCTGGAGTATTGA

> Primer1 (SEQ ID NO:103)
TTTCTTCTTTCGAGTTTCTATATCCGTCGCTG
> Primer2 (SEQ ID NO:104)
TTATCTGGAGTATTGATGAGCGCAC

METHOD FOR SYNTHESIS OF POLYNUCLEOTIDES USING A DIVERSE LIBRARY OF OLIGONUCLEOTIDES

CROSS-REFERENCE TO RELATED APPLICATIONS

This application is the U.S. national stage of International Patent Application No. PCT/EP2018/078016, filed on Oct. 15, 2018 and entitled A NOVEL METHOD FOR SYNTHESIS OF POLYNUCLEOTIDES USING A DIVERSE LIBRARY OF OLIGONUCLEOTIDES, which claims the benefit of priority under 35 U.S.C. § 119 from European Patent Application No. 17196317.6, filed Oct. 13, 2017. The disclosures of the foregoing applications are incorporated herein by reference in their entirety.

SEQUENCE LISTING

The entire content of a Sequence Listing titled "Sequence_Listing.txt," created on Mar. 16, 2020 and having a size of 20 kilobytes, which has been submitted in electronic form in connection with the present application, is hereby incorporated by reference herein in its entirety.

FIELD OF THE INVENTION

The invention relates to a novel method for synthesizing a double stranded (ds) polynucleotide having a predefined sequence using a diverse library of oligonucleotides.

BACKGROUND OF THE INVENTION

Artificial synthesis of polynucleotides is currently achieved through two kinds of methods that are not necessarily exclusive:

The first class of methods for the synthesis of polynucleotides is "chemical synthesis". This is a process through which single stranded DNA (or RNA) molecules are built by sequentially linking nucleotides, one by one, using phosphoramidite chemistry (Beaucage and Caruthers, 1981). This method allows for building of DNA molecules that have specific, predetermined template sequences of any complexity. Chemical methods are popular due to their inexpensive nature, are easily parallelizable and in some implementations allow for high-throughput production of DNA or RNA in chips (LeProust et al., 2010). The main and utmost disadvantage of these methods is that the yield of the reaction decreases dramatically with the length of the template being synthesized, limiting the size of the molecules, typically, to roughly 200 base-pairs (bp, or bps).

The second class of methods for DNA synthesis are the "assembly methods", which consist of biochemically joining oligonucleotides and polynucleotides of different sizes and of varying sequences in specific ways in order to obtain a larger molecule that has the desired target sequence. The source of these oligonucleotides is often chemical synthesis, but can also be products of enzymatic digestions of naturally occurring DNAs. These assembly methods are often commercialized under the product name "Gene Synthesis", a term that is a metonym for the synthesis of large polynucleotide chains (1K-5K bp), but not necessarily of gene-size length. There are several approaches reported in the literature for assembling smaller polynucleotides into the target sequence (Stemmer et al., 1995; Smith et al., 2003; Engler et al., 2008; Gibson et al., 2009; Horspool 2010)

In the past few years "Gibson Assembly" (Gibson et al., 2009) has become a popular method for linking several linear ds DNA fragments (size ranging from about 30 bp up to several Kbp). The method consists of joining many ds DNA fragments that have pairwise overlapping sequence homology. The overlapping homology region between fragments can range between about 15 to 80 bp. No overhangs are necessary, since the enzymatic machinery of the method takes care of producing the overhangs, fill in the gaps and correctly ligate the fragments. This enzymatic machinery makes use of three enzymes: T5 exonuclease, Phusion DNA polymerase and Taq DNA ligase, all in an isothermal reaction. The method is simple and versatile and can produce both linear and circular ds DNA products. The downside of this method is its limitation for automation making it unsuitable for large-scale commercial use.

The common theme in building DNA molecules of thousands of base pairs is to chemically synthesize small fragments of up to few hundred nt or bp and then concatenate these together by cloning, ligation, PCA or Gibson assembly.

Some approaches are suggestive of pre-constructing, possibly through chemical synthesis, a library of oligonucleotides that covers the possible genetic space, or a required subset of it.

Chari and Church propose using synthesized oligonucleotides (200 bases) to produce short DNA fragments and assembly into large DNA segments using in vivo homologous recombination in yeast and E. coli (Chari and Church, 2017).

WO 2009/138954 A2 discloses a method for synthesis of larger polynucleotides by solid phase assembly, wherein defined subunits required for assembly of the larger polynucleotide are chemically synthesized according to need.

Pedersen et al. (US2016/0215316A1) propose using a library comprising the space of all possible hexamers (N=4, 096 oligos). The six base pair long oligos are then assembled using oligo linkers to form polynucleotides. There are certain limitations pertaining to the concatenation of the oligonucleotides and large-scale DNA synthesis. Because it takes a suitably designed library and manual protocols such as for cloning, employing large volumes of reagents, methods are time consuming. These in turn add substantial costs to the price of synthesis, which increases per bp as the target sequence length increases.

WO2002/081490 discloses an approach utilizing the results of genomic sequence information by computer-directed polynucleotide assembly based upon information available in databases such as the human genome database. Specifically, it discloses a method of producing a target polynucleotide wherein the target polynucleotide is parsed into a series of contiguous oligonucleotides by a computer program and said target polynucleotide is generated by sequentially adding de novo synthesized oligonucleotides to an initiating oligonucleotide in a uni- or bidirectional manner.

WO2004/033619 also discloses an approach utilizing the results of genomic sequence information for computer-directed polynucleotide assembly.

Although the last few years have seen considerable progress in the techniques for synthesizing DNA, there are still severe restrictions in terms of volume, throughput and, specially, length of DNA.

SUMMARY OF THE INVENTION

It is the object of the present invention to provide an improved method for synthesizing double stranded (ds) polynucleotides, aiming to shorten the time to synthesize a target ds polynucleotide.

The object is solved by the subject of the present invention.

According to the invention there is provided a method for synthesizing a target ds polynucleotide having a predefined sequence, comprising a) providing an oligonucleotide library within an array device, which comprises a diversity of oligonucleotide library members, wherein each of the library members has a different nucleotide sequence and is contained in a separate library containment in an aqueous solution, which diversity includes single stranded oligonucleotides (ss oligos) and double stranded oligonucleotides (ds oligos) with at least one overhang and covers at least 10.000 pairs of matching oligonucleotides, b) in a first step, transferring at least a first pair of matching oligonucleotides from said library into a first reaction containment using a liquid handler and assembling the matching oligonucleotides thereby obtaining a first reaction product comprising at least one overhang, c) in a second and further steps, transferring at least a second and further pairs of matching oligonucleotides from said library into a second and further reaction containments, respectively, using a liquid handler and assembling the matching oligonucleotides thereby obtaining a second and further reaction products each comprising at least one overhang, respectively, d) assembling said first, second and further reaction products in a predetermined workflow, thereby producing said target ds polynucleotide with an overhang, optionally followed by a finalization step to prepare blunt ends, wherein said pairs of matching oligonucleotides and assembly workflow are determined using an algorithm to produce said target ds polynucleotide.

Specifically, a series of different target ds polynucleotides are synthesized using the same oligonucleotide library. Specifically, said different target ds polynucleotides have different sequences and are not fragments of each other.

Specifically, said different target ds polynucleotides have a sequence identity of less than 50%, preferably less than 30%. Specifically, said different target ds polynucleotides have a sequence identity of less than 49, 48, 47, 46, 45, 44, 43, 42, 41, 40, 39, 38, 37, 36, 35, 34, 33, 32, 31, 30, 29, 28, 27, 26, 25, 24, 23, 22 or 21%. Even more preferably, said different target ds polynucleotides have a sequence identity of less than 20 or 10% to each other, specifically they have a sequence identity of less than 19, 18, 17, 16, 15, 14, 13, 12, 11, 9, 8, 7, 6 or 5%.

Specifically, said target ds polynucleotide is a DNA molecule.

Specifically, one or more amplification steps are performed, e.g. by performing a PCR, preferably of 25 cycles. Specifically, said PCR employs a HiFi thermostable DNA Polymerase (Phusion or Q5) and two oligonucleotides complementary to each of the overhangs of the assembled fragment, and said complementary oligonucleotides including cleavage sites for TypeIIS restriction enzyme (BfuAI). Specifically, the amplified product is contacted with the TypeIIS restriction enzyme, which introduces the original overhangs into the amplified fragments. Specifically, said amplification step is carried out after any one or more of the first, second, third or further assembly steps, wherein the first, second, third or further reaction products, respectively, are amplified. Specifically, said amplification step is carried out after assembly of the target ds polynucleotide, wherein the target ds polynucleotide is amplified.

Specifically, the predetermined workflow (also referred to as "assembly workflow") is a hierarchic one, which is specifically characterized as follows:

A hierarchic workflow shall mean parallel or separate production of intermediary assembled matching pairs of polynucleotides which are produced as intermediates, each of the intermediates being assembled in a separate reaction compartment, which intermediates are further assembled to obtain the target polynucleotide or a part thereof. According to a specific example, in a first step, matching pairs of oligonucleotides are combined in parallel and in independent reaction compartments thereby producing in each compartment a polynucleotide that has the combined size of the reagent oligonucleotides and the same overhang length as the reagent oligonucleotides. In a second and subsequent steps, this process is repeated iteratively by using the previous products or other oligonucleotides as reagents thereby producing in each tier a polynucleotide of the combined size of the reagent polynucleotides that maintains the same overhang size. If the step before the last has three compartments, first reacting only two of the compartments carrying matching pairs, and then a further reaction step between this product and the last compartment will produce the target polynucleotide. Alternatively, if the three compartments contain polynucleotides that can form only two matching pairs in total, combining the three compartments the target polynucleotide is produced.

Specifically, the assembly workflow is automated. Specifically, the automated workflow employs microfluidic handlers that are capable of transferring serially or in parallel the full or partial contents of one or several compartments into other pre-specified compartments that may or may not be empty.

Specifically, the assembly workflow is sequence-dependent, meaning that the specific order is determined by the sequence of a template such that when matching pairs are combined at any step in the workflow they result in a larger part of the target ds polynucleotide or finally in the target ds polynucleotide. Specifically, the workflow is determined according to the sequence of a template or the sequence of the target ds polynucleotide.

Specifically, by the method described herein polynucleotides of lengths up to 1.000, 5.000, 10.000 or 100.000 base pairs (bp) or even longer can be produced at a low price and at a high speed.

The method described herein specifically comprises the following components:

A) A pre-built library of oligonucleotides that can be designed to cover the whole genetic sequence space and organizes the oligos in space for an efficient access by a liquid handler or microfluidics device. The access is considered efficient, if the spatial organization of the library diminishes the time needed to access necessary oligonucleotides. Specifically, said access is considered efficient if it diminishes or reduces the total handling time of the library, wherein said total handling time is the time spent handling library members during the synthesis of a target ds polynucleotide. Specifically, said access is further considered efficient if it diminishes the operational costs or diminishes the amount of necessary consumables associated with the access to the oligonucleotides, as compared to other organizations, in particular to spatially randomly placed oligonucleotides or lexicographical ordering. Specifically, the access is considered efficient, if the total handling time of the library is reduced at least by 5, 10, 15, 20, 25 or 50% compared to the total handling time of a randomly or lexicographically organized library.

B) A sequence-specific hierarchical assembly workflow, determined by an algorithm, to produce the long polynucleotide without mismatches.

The library described herein specifically comprises single stranded (ss) and double stranded (ds) oligonucleotides (oligos), also referred to as library members. These library members are pre-built, provided in storage stable solutions, and located at defined positions within the array device. Oligos of the library are synthesized and stored in the array device until needed.

Specifically, the oligonucleotides are linear polymers of nucleotide monomers and comprise "A" denoting deoxyadenosine, "T" denoting deoxythymidine, "G" denoting deoxyguanosine, and "C" denoting deoxycytidine or besides conventional bases (A, G, C, T) can comprise nucleotide-analogs e.g., inosine and 2'-deoxyinosine and their derivatives (e.g. 7'-deaza-2'-deoxyinosine, 2'-deaza-2'-deoxyinosine), azole- (e.g. benzimidazole, indole, 5-fluoroindole) or nitroazole analogues (e.g. 3-nitropyrrole, 5-nitroindole, 5-nitroimidazole, 4-nitropyrazole, 4-nitrobenzimidazole) and their derivatives, acyclic sugar analogues (e.g. those drived from hypoxanthine- or indazole derivatives, 3-nitroimidazole, or imidazole-4,5-dicarboxamide), 5'-triphosphates of universal base analogues (e.g. derived from indole derivatives), isocarbostyril and its derivatives (e.g. methylisocarbostyril, 7-propynylisocarbostyril), hydrogen bonding universal base analogues (e.g. pyrrolopyrimidin), and other chemically modified bases (such as diaminopurine, 5-methylcytosine, isoguanine, 5-methyl-isocytosine, K-2'-deoxyribose, P-2'-deoxyribose) or e.g. others modified bases which can have different base-pairing preferences and can pair with more than one natural nucleobase with similar stringency/probability. The monomers are linked by phosphodiester linkage or in certain cases, by peptidyl linkages or by phosphorothioate linkages or by any of the other types of nucleotide linkages.

Specifically, the single stranded DNA oligonucleotide library members (herein simply referred to as ss oligos) are or comprise natural nucleosides (e.g. adenosine, thymidine, guanosine, cytidine, uridine, deoxyadenosine, deoxythymidine, deoxyguanosine, and deoxycytidine); nucleoside analogs (e.g., inosine, or 5-methylisocytosine, or 3-nitropyrrole, 5-nitroindole, pyrrolidine, 4-nitroimidazole, 4-nitropyrazole, 4-nitrobenzimidazole, 4-aminobenzimidazole, 5-nitroindazole, 3-nitroimidazole, 5-aminoindole, benzimidazole, 5-fluoroindole, indole, methylisocarbostyril, pyrrolopyrimidine 7-propynylisocarbostryril, 2-aminoadenosine, 2-thiothymidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-amino-adenosine, 7-deaza-adenosine, 7-deaza-guanosine, 8-oxoadenosine, 8-oxoguanosine, 0(6)-methylguanine, and 2-thiocytidine); chemically or biologically modified bases (including methylated bases); intercalated bases; modified sugars (e.g., ribose, 2'-deoxyribose, arabinose, and hexose); and/or modified phosphate groups (e.g., phosphorothioates and 5'-N-phosphoramidite linkages).

Specifically, the double stranded DNA oligonucleotide library members (herein simply referred to as ds oligos) are or comprise natural nucleosides (e.g. adenosine, thymidine, guanosine, cytidine, uridine, deoxyadenosine, deoxythymidine, deoxyguanosine, and deoxycytidine); nucleoside analogs (e.g., inosine, or 5-methylisocytosine, or 3-nitropyrrole, 5-nitroindole, pyrrolidine, 4-nitroimidazole, 4-nitropyrazole, 4-nitrobenzimidazole, 4-aminobenzimidazole, 5-nitroindazole, 3-nitroimidazole, 5-aminoindole, benzimidazole, 5-fluoroindole, indole, methylisocarbostyril, pyrrolopyrimidine 7-propynylisocarbostryril, 2-aminoadenosine, 2-thiothymidine, 3-methyl adenosine, 5-methylcytidine, 2-aminoadenosine, C5-bromouridine, C5-fluorouridine, C5-iodouridine, C5-propynyl-uridine, 05-propynyl-cytidine, C5-methylcytidine, 2-amino-adenosine, 7-deaza-adenosine, 7-deaza-guanosine, 8-oxoadenosine, 8-oxoguanosine, 0(6)-methylguanine, and 2-thiocytidine); chemically or biologically modified bases (including methylated bases); intercalated bases; modified sugars (e.g., ribose, 2'-deoxyribose, arabinose, and hexose); and/or modified phosphate groups (e.g., phosphorothioates and 5'-N-phosphoramidite linkages) and are formed by annealing fully or partially complementary single stranded oligonucleotides.

Specifically, the oligonucleotide library members can be produced by any of the chemical polynucleotide (oligonucleotide) synthesis methods, including the H-phosphonate, phosphodiester, phosphotriester or phosphite triester synthesis methods or any of the massively parallel oligonucleotide synthesis methods, e.g. microarray or microfluidics-based oligonucleotide synthesis (e.g. as described in References (Gao et al. 2001) (LeProust et al. 2010) (Bonde et al. 2014a)).

Specifically, the oligonucleotide library members can be produced by any of the enzymatic polynucleotide (oligonucleotide) synthesis methods, including ssDNA synthesis by DNA polymerase proteins or by reverse transcriptase proteins, which produce hybrid RNA-ssDNA molecules. Specifically, the enzymatic polynucleotide synthesis reaction can occur in vivo or in vitro.

Specifically, the oligonucleotide library members are produced by synthesizing the oligonucleotide sequence from nucleotide building blocks by any of the polynucleotide synthesis methods, wherein the building blocks are comprised of "A" denoting deoxyadenosine, "T" denoting deoxythymidine, "G" denoting deoxyguanosine, or "C" denoting deoxycytidine or other natural nucleosides (e.g. adenosine, thymidine, guanosine, cytidine, uridine), nucleotide-analogs e.g., inosine and 2'-deoxyinosine and theirs derivatives (e.g. 7'-deaza-2'-deoxyinosine, 2'-deaza-2'-deoxyinosine), azole- (e.g. benzimidazole, indole, 5-fluoroindole) or nitroazole analogues (e.g. 3-nitropyrrol, 5-nitroindol, 5-nitroimidazole, 4-nitropyrazole, 4-nitrobenzimidazole) and their derivatives, acyclic sugar analogues (e.g. those derived from hypoxanthine- or indazole derivatives, 3-nitroimidazole, or imidazole-4,5-dicarboxamide), 5'-triphosphates of universal base analogues (e.g. derived from indole derivatives), isocarbostyril and its derivatives (e.g. methylisocarbostyril, 7-propynylisocarbostyril), hydrogen bonding universal base analogues (e.g. pyrrolopyrimidine), or any of the other chemically modified bases (such as diaminopurine, 5-methylcytosine, isoguanine, 5-methyl-isocytosine, K-2'-deoxyribose, P-2'-deoxyribose). The building blocks are linked by phosphodiester linkage or peptidyl linkages or by phosphorothioate linkages or by any of the other types of nucleotide linkages.

In a specific embodiment of the invention, said ss oligos have a length of 6 to 26 nucleotides. Preferably, ss oligos have a length of at least 6, 7, 8, 9, 10, 11, 12, 13, 14 or 15 nucleotides. Preferably, ss oligos have a length of maximum 26, 25, 24, 23, 22, 21, 20, 19, 18, 17 or 16 nucleotides. In a further specific embodiment said ss oligos have a length of more than 26 nucleotides. Preferably, ss oligos have a length of less than 100, 90, 80, 70, 60 or 50 nucleotides.

Specifically, ds oligo library members have at least one overhang. An overhang is specifically characterized by a reactive (i.e. capable of hybridizing with another ss oligo or overhang) ss terminal stretch of one or more nucleotides which is part of and/or extending a ds oligo or polynucleotide.

The library specifically comprises ds oligos with one overhang and a blunt end. A blunt end is specifically characterized by a ds terminal stretch of one or more base pairs which is part of a ds oligo or polynucleotide.

Specifically, ds oligos with overhangs on both ends and no blunt end may be comprised in the library.

Specifically, ds oligos have a length of 6 to 26 base pairs, and said overhang is not more than half of the respective ds oligo length. Specifically, ds oligos have a length of at least 6, 7, 8, 9, 10, 11, 12, 13, 14 or 15 base pairs. Specifically, ds oligos have a length of maximum 26, 25, 24, 23, 22, 21, 20, 19, 18, 17 or 16 base pairs. Specifically, if said ds oligo is 6 base pairs long, the overhang is not more than 3 nucleotides long. Specifically, if said ds oligo is 24 base pairs long, the overhang is not more than 12 nucleotides long. In a further specific embodiment said ds oligos have a length of more than 26 base pairs. Preferably, ds oligos have a length of less than 100, 90, 80, 70, 60 or 50 base pairs.

The library described herein is specifically constituted by physical oligonucleotides and synthesized in standardized conditions. Oligonucleotides are purified, may comprise modifications and are ideally kept at a standard concentration and volume in an appropriate buffer and/or excipient, so that they are ready-to-use.

Specifically, any of the following buffer and/or excipients may be used to keep the oligos in solution: Tris Buffer, T.E. Buffer (Tris-EDTA Buffer) or Nuclease Free Water. Specifically, library members may be kept in Tris Buffer, wherein said Tris Buffer is provided at a concentration of about 10 mM (+/−1 mM or 2 mM). Specifically, library members may be kept in T.E. Buffer. Specifically, said T.E. Buffer is at least composed of Tris, at a concentration of about 10 mM (+/−1 mM or 2 mM), and EDTA, at a concentration of any one of 0.1, 0.2, 0.3, 0.4, 0.5, 0.6, 0.7, 0.8, 0.9 or 1.0 mM. Specifically, Nuclease Free Water, is water which has been de-ionized, filtered and autoclaved and is essentially free of contaminating non-specific endonuclease, exonuclease and RNase activity.

Specifically, all library members are kept in the compartmented array device, using the same or different buffer and/or excipients in each case.

The library described herein may comprise thousands of oligos. Specifically, the library described herein comprises a diversity of oligonucleotide library members, wherein each of the library members has a different nucleotide sequence and which diversity covers at least 10.000 pairs of matching oligonucleotides. Specifically, the library comprises at least 20.000, 30.000, 40.000, 50.000, 60.000, 70.000, 80.000, 90.000 or 100.000 pairs of matching oligonucleotides. Specifically, the library contains enough pairs of matching oligonucleotides to cover the whole sequence space.

The pairs of matching oligonucleotides described herein refer to single stranded oligonucleotides comprising partially or fully complementary sequences. Said pairs of matching oligos may be present in the library as ss oligos in separate containments or two or more complementary ss oligos may be contained in one containment where they may anneal and form ds oligos. The nucleotide sequences of a pair of matching ss oligos may be complementary in at least 1, 2, 3, 4, 5, 6, 7, 8, 9, 10, 11, 12, 13, 14, 15, 16, 17, 18, 19, 20, 21, 22, 23, 24, 25 or 26 nucleotides, such that a matching pair can form a new ds polynucleotide molecule by hybridization of the ss oligo sequences, preferably wherein the ss oligos hybridize in part, thereby obtaining a ds polynucleotide with an overhang.

An ss oligo may specifically be part of a matching pair consisting of two or three hybridization partners. Specifically, an ss oligo can be used as a first hybridization partner capable of hybridizing with a second hybridization partner, which is another ss oligo or a ds oligo with a complementary overhang.

Specifically, an ss oligo can be used as a first hybridization partner capable of hybridizing with two different ss and/or ds oligos, or two different ds polynucleotides, which are used as second and third hybridization partners. Specifically, the first hybridization partner is a matching ss oligo, wherein a first part of the ss oligo is hybridizing to a second hybridization partner, and a second part of the ss oligo is hybridizing to a third hybridization partner, thereby obtaining one ds polynucleotide composed of the three hybridization partners without a gap.

A pair of matching ds oligos is specifically characterized by complementary sequences in the respective overhangs of the ds oligos, e.g. wherein the respective overhangs are complementary in at least 1, 2, 3, 4, 5, 6, 7, 8, 9, 10, 11, 12, 13, 14, 15, 16, 17, 18, 19, 20, 21, 22, 23, 24, 25 or 26 nucleotides, such that the matching pair can form a new ds polynucleotide molecule by hybridization of the overhang sequences.

The library described herein may specifically comprise a diversity of double stranded oligonucleotides library members, wherein each of the ds oligo library members has a different nucleotide sequence. Specifically, said diversity covers at least 100, 500, 1.000, 2.000, 3.000, 4.000, 5.000, 10.000, 20.000, 40.000, 60.000, 80.000, 100.000, 120.000, 140.000, 160.000, 180.000 or 200.000 different ds oligos.

The library described herein may specifically comprise a diversity of single stranded oligonucleotides library members, wherein each of the ss oligo library members has a different nucleotide sequence. Specifically, said diversity covers at least 100, 500, 1.000, 2.000, 3.000, 4.000, 5.000, 10.000, 20.000, 40.000, 60.000, 80.000, 100.000, 120.000, 140.000, 160.000, 180.000 or 200.000 different ss oligos. Specifically, said ss oligos may be used as linkers, specifically in the assembly of a ds polynucleotide.

Specifically, said diversity means, different library members differ in at least one base or base pair. One library member may actually encompass multiple copies of ss or ds oligonucleotides of the same sequence. Such multiple copies of a library member are specifically contained in only one library containment.

In a specific embodiment of the invention, said diversity covers ss oligos and/or ds oligos which are phosphorylated. Specific embodiments refer to ss oligos or ds oligos which are modified by any one or more of phosphorylation, methylation, biotinylation, or linkage to a fluorophore or quencher. Therefore, the library described herein comprises library members which can be any or all of unmodified ss oligos, phosphorylated ss oligos, methylated ss oligos, biotinylated ss oligos, phosphorylated, biotinylated and methylated ss oligos, unmodified ds oligos, phosphorylated ds oligos, methylated ds oligos, biotinylated ds oligos and phosphorylated, biotinylated and methylated ds oligos. Preferably, library members comprise a 5' phosphorylation. Specifically, the library described herein further comprises ss oligos comprising fluorophores or quenchers and ds oligos comprising fluorophores or quenchers.

In a specific embodiment of the invention, the oligonucleotide library is provided within an array device and library members are contained in separate library containments, each in an aqueous solution. Specifically, said array device is any of a microliter plate, a microfluidic microplate, a set of capillaries, a microarray or a biochip, preferably a DNA and/or RNA biochip. Said array device may comprise only one, all or any number of the aforementioned containments.

In a further specific embodiment of the invention, more than one different library members may be contained in only one library containment. Specifically, said different library members contained in one library containment are ss oligos of such a sequence that they are not capable of annealing to each other. Specifically, said different library members contained in one library containment are ds oligos of such a sequence that they are not capable of ligating to the other ds oligos contained therein. Specifically, said different library members contained in one library containment are ss oligos and ds oligos of such a sequence that they are not capable of annealing to each other.

In a specific embodiment, said separate library containments are spatially arranged in a three-dimensional order, wherein the individual compartments are located within a device at defined coordinates within the x-, y- and z-axes. Specifically, said three-dimensional order comprises at least any one of two, three, four, five, six, seven, eight, nine, ten, fifteen, twenty, thirty, forty, fifty, sixty or even more stacked library containments, which are at least partially or fully stacked. Preferably, the library containments are placed in different lays, which are laid one above the other in different lays. Specifically, the lays are placed at predefined positions within the three-dimensional order. Preferably, each of said library containments within one lay comprises a series of library members spatially arranged in a two-dimensional order at predefined positions.

Specifically, the three-dimensional order is predefined by a parameter which primarily serves to shorten synthesis time. Preferably, said parameter is frequency of use, placing those oligos in close proximity to each other which frequently form a matching pair in DNA sequences, e.g. naturally occurring or commonly used in target ds polynucleotides or fragments thereof. Due to the large number of oligos required to build any given sequence, most spatial distributions of oligos in the library would incur into wasted time and resources due to the time needed to scan the library and search for the desired oligos. However, by using a specific distribution of the oligos, there is minimal movement of an automatic device to transfer the pairs of matching oligos into a reaction containment. For example, oligos can be stored in micro-well plates, where the first plate contains the most common matching pairs of oligonucleotides and further plates are arranged in decreasing order until the last plate contains the least frequently used oligos.

In the method described herein, oligonucleotides from the library described herein are transferred into a reaction containment using a liquid handler. Specifically, said liquid handler may be a microdroplet handler. Specifically, the liquid handler is automated. Using a liquid handler, a suitable volume of at least any one of 10, 20, 30, 40, 50, 60, 70, 80, 90 100, 200 or 500 nL can be transferred, e.g. such that at least any one of $10^9$, $10^{10}$, $10^{11}$ or $10^{12}$ copies of a library member, such as single stranded oligonucleotides, matching pairs of single stranded oligonucleotides and double stranded oligonucleotides, are placed into one reaction containment. Preferably, at least about $10^{11}$ copies (e.g. $6.06 \times 10^{11}$ copies) of a specific oligo are placed into one reaction containment to react with another oligo. Preferably, the volume in which oligos are transferred by the liquid handler is between 10 and 1000 nL. More preferably it is between 10 and 500 nL and even more preferably it is between 50 and 250 nL.

Specifically, a reaction containment is a compartment unit, such as a well, of any one of a microtiter plate, a microfluidic microplate, a set of capillaries, a microarray or a biochip, preferably a DNA and/or RNA biochip. Specifically, reaction containments feature an environment in which one nucleic acid strand bonds to a second nucleic acid strand by complementary strand interactions and hydrogen bonding to produce a double stranded oligonucleotide. Such conditions include the chemical components and their concentrations (e.g., salts, chelating agents, formamide) of an aqueous or organic solution containing the nucleic acids, and the temperature of the mixture. Other well-known factors, such as the length of incubation time or reaction chamber dimensions may contribute to the environment.

According to the method provided herein, oligonucleotides are transferred from the library into a reaction containment and assembled to obtain a reaction product. Specifically, said assembly is by any method of hybridizing ss nucleotide sequences, and/or a ligation reaction which is an enzymatic and/or chemical reaction. Specifically, said ligation reaction is an enzymatic ligation reaction using ligase, or ribozymes capable of ligation reaction. Preferably T4 DNA ligase, T7 DNA Ligase, T3 DNA Ligase, Taq DNA Ligase, DNA polymerase, or engineered enzymes are used in the ligation reaction. Preferably, the following ligation reaction is used: T4 DNA Ligase, at a concentration of 10 cohesive end units per μL supplemented with 1 mM ATP (Sambrook and Russel, 2014, Chapter 1, Protocol 17).

Specifically, said assembly is directly by hybridizing matching overhangs, or indirectly by hybridizing a suitable ss oligo linker, which ss oligo linker is an ss oligo contained in said library which is selected and transferred from said library to assemble any of said first, second or further reaction products.

Oligonucleotides are specifically assembled according to a defined workflow. The workflow is specifically designed to avoid mismatches or reaction products which cannot be used for assembly to produce the target ds polynucleotide. If there are partial constructs that can anneal in alternative ways, a runaway, i.e. an uncontrolled polymerization reaction, can occur. To avoid combinations of pairs of matching oligonucleotides that would result in unwanted constructs or runaway reactions, pairs of matching oligonucleotides are assembled in a predetermined sequence of assembly steps, i.e. a specific workflow. Preferably, said specific workflow is not linear but hierarchical, i.e. following an algorithm that provides for intermediate reaction products which are defined non-consecutive parts of the target ds polynucleotide conveniently produced avoiding undesired reaction products to the extent possible, before such intermediate reaction products are further assembled into further intermediate reaction products or into the target ds polynucleotide sequence.

In a linear workflow, the polynucleotide is assembled in a linear fashion starting at the 3' end of the leading strand, and adding the next oligo to link the 3' end of the leading strand with the 5' end of the next oligo. For example, oligo B is ligated to oligo A, oligo C is ligated to oligo B, oligo D is ligated to oligo C and so forth. This assembly may be achieved simultaneously by adding all oligos to the reaction containment at the same time, or the polynucleotide is extended progressively by successively adding oligos A, B, C, D and so forth to the reaction containment.

A hierarchical workflow may, for example, be necessary when oligo D is capable not only of ligating to oligo C but also to oligo A due to complimentary sequences or overhangs. A linear workflow as described above would result in the unwanted polynucleotide A-D-B-C-D in addition to the desired polynucleotide A-B-C-D. Therefore, the polynucleotide is preferably assembled in a hierarchical workflow. Accordingly, in two separate reaction containments oligos A and B and oligos C and D are ligated, respectively. The ligation reaction will yield the reaction products A-B and C-D which can then be transferred into a third reaction containment, wherein upon ligation the desired polynucleotide A-B-C-D is formed.

Specifically, said workflow is determined using an algorithm. Specifically, said algorithm selects pairs of matching oligonucleotides and ss oligo linkers, if necessary, and determines the assembly workflow, not by a mere sequence partitioning, but by determining an optimal or near-optimal way to assemble the target ds polynucleotide, avoiding mismatches or undesired reaction products as far as possible. Pairs of matching oligonucleotides and assembly workflow are specifically selected to avoid undesired (incorrect) reactions or reaction products, such as palindromic sequences, runaway reactions and unambiguous assembly. If there are incorrect reaction products besides the correct reaction products, such incorrect reaction products are suitably separated from the correct ones e.g. as follows: using gel electrophoresis to detect oligonucleotides or polynucleotides of a certain size and excising and purifying bands of the gel corresponding to the size of the desired reaction product. Specifically, correct reaction products can be detected by incorporation of tags or labels into the sequence. Specifically, oligos may be captured using biotinylated oligonucleotide adapters capable of hybridizing with the overhang of the oligo wherein, said adapters are fixed to the substrate and coated with streptavidin. Non-captured incorrect products are eliminated by washing and subsequently, the correct products are released from the adapters by increasing the temperature. Specifically, further separation methods well known in the art may be applied. Specifically, such methods may involve chromatographic or affinity separation methods.

In a specific embodiment of the invention, said target ds polynucleotide has a length of at least 48 nucleotides. Specifically, said target ds polynucleotide has a length of at least any one of 100, 200, 300, 400, 500, 1.000, 10.000, 100.000, 200.000 or 500.000 nucleotides.

Typically, a template is used as a model to synthesize the target ds polynucleotide. Specifically, the nucleotide sequence of said target ds polynucleotide is identical to the nucleotide sequence of a template.

In a specific embodiment, a sequence of interest (SOI) is provided as a single stranded template and/or translated into two single stranded template sequences, based on which the target ds polynucleotide is synthesized. In a certain embodiment, a first template comprises the sequence of the SOI, and a second template comprises the reverse complement to the SOI.

In a further embodiment of the invention, said target ds polynucleotide is a proxy ds polynucleotide which has a sequence that is identical to said template, which proxy ds polynucleotide is further modified to obtain a polynucleotide which has a sequence of interest (SOI) which is different from the sequence of the target ds polynucleotide. Typically, the proxy ds polynucleotide is produced as an intermediate product, wherefrom a ds polynucleotide characterized by the SOI can be produced by one or more further steps of mutagenesis.

Specifically, the sequence of said template, according to which said proxy ds polynucleotide is synthesized, is not identical to said SOI. Specifically, the sequence of said template is less than any one of 100, 99, 98, 97, 96, 95, 94, 93, 92, or 91% identical, and/or at least any of 90, 91, 92, 93, 94, 95, 96, 97, 98, or 99% identical to said SOI.

In a specific embodiment of the method provided herein, the terminal nucleotides of the 3' or 5' end, or of both ends of the sequence of one strand, or each of the ds strands are removed before partitioning into shorter sequences. Specifically they are removed computationally. Thereby, a template is produced which is different from the SOI. Specifically, any one of 1, 2, 3, 4, 5, 6, 7, 8, 9, 10, 11, 12, 13, 14, 15, 16, 17, 18, 19, 20, 21, 22, 23, 24 or 25 of the terminal nucleotides are removed, of the 3' end, or of the 5' end of the sequence to produce the template. Specifically, said nucleotide(s) are removed to generate overhangs and/or to prepare for finalization of synthesis by producing blunt ends at each of the termini of the target ds polynucleotide.

Specifically, the template is comprised of a single stranded or double stranded sequence. Preferably, said template is single stranded. Specifically, said two single stranded template sequences are aligned generating a double stranded template. Specifically, the sequence of said template is partitioned into shorter sequences, sub-sequences comprising oligonucleotide library members, and positions of said library members in the library are digitally annotated. Specifically, partitioning into sub-sequences depends on the hierarchical workflow and on the library members present in the library.

Specifically, the target ds polynucleotide has blunt ends on both ends.

Specifically, the method provided herein comprises a finalization step.

Specifically, said finalization step serves to add one or more nucleotide(s) which correspond to those previously removed from the 3' end and 5' end, respectively, to prepare the template, aiming to generate blunt ends. Specifically, oligos from the library are selected, which are complementary to the nucleotides at the 3' end and 5' end, respectively, i.e. complementary to the sticky ends of the polynucleotide. Specifically, these oligos are used as primers in a PCR reaction which is prepared to amplify the final product and to add the remaining nucleotides to each strand to synthesize the complete target polynucleotide with blunt ends.

Specifically, said finalization step comprises a purification step of the PCR product employing standard kits, such as the Monarch PCR & DNA clean up kit from New England Biolabs (product nr. T1030), to eliminate remaining oligos, enzymes and reagents, leaving the target ds polynucleotide as a DNA product, ready for downstream applications.

Alternatively, one or both blunt ends of the target ds polynucleotide can be produced by selecting a matching ds oligo with blunt ends or by selecting a ss oligo which is complementary to an overhang, and hybridizing without generating any further overhang thereby producing a blunt end.

Specifically, said nucleotide sequence of a target ds polynucleotide, SOI or template can be of natural or artificial origin.

In order to produce a ds polynucleotide, which has a complicated SOI, in a simpler and thus quicker assembly workflow, a proxy ds polynucleotide with a target sequence less than 100% identical to the SOI may be produced. Said proxy ds polynucleotide produced by the assembly method described herein can then be further modified to produce a ds polynucleotide with a nucleotide sequence 100% identical to the nucleotide sequence of the SOI. Specifically, said proxy ds polynucleotide is further modified by any of directed mutagenesis, endonucleases or exonucleases to obtain a nucleotide sequence identical to the nucleotide sequence of said template.

In a further specific embodiment of the invention, the target ds polynucleotide is further modified to produce a derivative thereof, which is any of a ds DNA, ss DNA or RNA molecule.

Specifically, said target ds polynucleotide is modified by site-directed mutagenesis, thereby introducing one or more point mutations which are any of nucleotide insertions, deletions or substitutions.

Specifically, said target ds polynucleotide is modified by enzymatic modification, employing any one or more of methyltransferases, kinases, CRISPR/Cas9, multiplex automated genome engineering (MAGE) using λ-red recombination, conjugative assembly genome engineering (CAGE), the Argonaute protein family (Ago) or a derivative thereof, zinc-finger nucleases (ZFNs), transcription activator-like effector nucleases (TALENs), meganucleases, tyrosine/serine site-specific recombinases (Tyr/Ser SSRs), hybridizing molecules, sulfurylases, recombinases, nucleases, DNA polymerases, RNA polymerases or TNases.

In a specific embodiment of the invention, said target ds polynucleotide is sequenced to verify the degree of identity with the sequence of a template or a SOI. Any suitable sequencing method may be used, for example any one of SNP genotyping methods, including hybridization-based methods (e.g. molecular beacons, SNP microarrays, restriction fragment length polymorphism, PCR-based methods, including Allele-specific PCR, primer extension-, 5'-nuclease or Oligonucleotide Ligation Assay, Single strand conformation polymorphism, Temperature gradient gel electrophoresis, Denaturing high performance liquid chromatography, High-resolution Melting of the entire amplicon (HRM), SNPlex and surveyor nuclease assay; Sequencing based mutation analysis, including capillary sequencing or high-throughput sequencing of an entire PCR amplicon of the PTR (amplicon sequencing). Such high-throughput (HT) amplicon sequencing methods include, but are not restricted to polony sequencing, pyrosequencing, Illumina (Solexa) sequencing, SOLiD sequencing, semiconductor sequencing, DNA nanoball sequencing, Heliscope single molecule sequencing, Single molecule real time (SMRT) sequencing, Nanopore DNA sequencing, tunnelling currents DNA sequencing, sequencing by hybridization, sequencing with mass spectrometry, Microfluidic Sanger sequencing, Microscopy-based sequencing, RNAP sequencing.

According to the invention provided herein, an oligonucleotide library is provided within an array device comprising a diversity of library members, which are single stranded oligonucleotides (ss oligos) and double stranded oligonucleotides (ds oligos) with at least one overhang, wherein each of the library members has a different nucleotide sequence and is contained in a separate library containment in an aqueous solution, which containments are spatially arranged in a three-dimensional order, which diversity covers at least 10.000 pairs of matching oligonucleotides.

Specifically, said library containments are spatially arranged in a three-dimensional order, preferably according to frequency of use, and wherein said three-dimensional order comprises at least any one of two, three, four, five, six, seven, eight, nine, ten, fifteen, twenty, thirty, forty, fifty, sixty or even more stacked library containments, which are at least partially or fully stacked.

Further, the invention provides for the use of the oligonucleotide library described herein for synthesizing a series of different target double stranded (ds) polynucleotides having a predefined sequence, wherein said different target double stranded (ds) polynucleotides have a sequence identity of less than 50%, preferably less than 30%.

FIGURES

Figure 1:
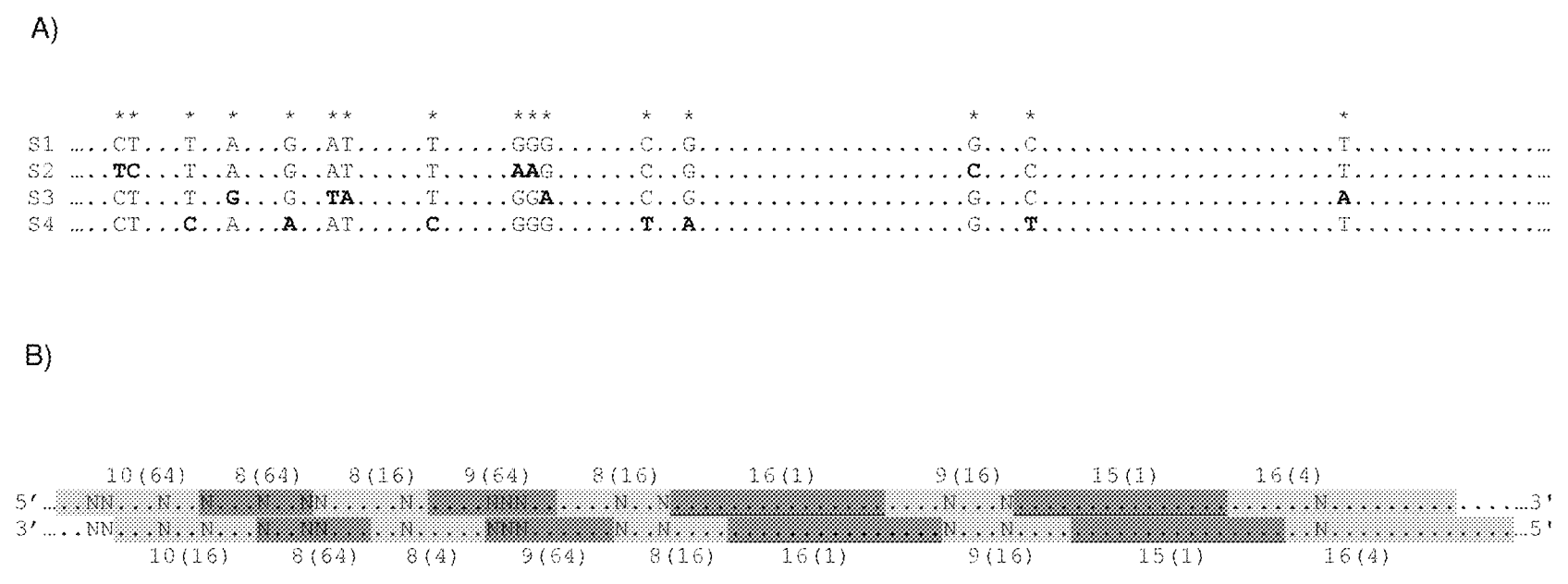

FIG. 1A. Source sequences used to construct a library (only fragment of 100 bp is shown), corresponding to four haplotypes of the hyper-variable region II of human mitochondria (Anderson et al., 1981: Gene Bank accession nr.: J01415).

FIG. 1B. Scaffold of the design of the oligos that are required to build any possible combination of haplotypes (assuming full heterozygocity of each polymorphic site). Both strands are shown. Each Z-shaped block is an oligo pair where N stands or any of the four bases A, T, G, or C. The number above and below each oligo sequence scaffold each oligo indicates the length of the oligo and in parenthesis the number of oligos that are to be present in the library to cover all possible haplotypes at the variable sites. Each ss oligo is to be stored individually in a compartment of the library, except those underlined that are to be stored as annealed pairs.

FIG. 2A. Nucleotide sequence of the SOI, called DISCOVER (SEQ ID NO: 1).

FIG. 2B. Nucleotide sequence of the 16 oligos constituting SOI DISCOVER.

FIG. 2C. Dimer structure of the constituting oligos. Here depicted for D+ and D−, but same structure applies to all other dimers.

FIG. 3. Location of oligos in a well plate.

FIG. 3A. After annealing, the contents of columns 1 and 3 are transferred to columns 2 and 4, respectively.

FIG. 3B. After incubation of the first ligation reaction, the contents of column 2 are transferred to column 4.

FIG. 3C. After incubation of the second ligation reaction, the contents of A4 are transferred to well B4 and incubated for the third and last ligation reaction. Well B4 contains the 128 bp target ds polynucleotide.

FIG. 4. Acrylamide gel (10%) showing the contents of the process described in Example 2. Lane 1: reactions D+I (well A2 in FIG. 2B). Lane 2: negative control (for ligation) with a 64 bp dsDNA. Lane 3: positive control (for ligation) with a 64 bp dsDNA. Lanes 4 and 5: reactions DI+SC (well A4 in FIG. 2C) in two dilutions. Lanes 6 and 7: target ds polynucleotide. Lane 8: 50 bp ladder (NEB).

FIG. 5A. Partial SOI and its reverse complement (positions 65-100; otherwise as in FIG. 1A). The elements in italic, bold and regular fonts indicate different dimers. The underlined portions highlight the self-complementary overhangs that have to be avoided. Upper sequence SEQ ID NO: 18; lower sequence SEQ ID NO: 19.

FIG. 5B. Partial sequence of the template for producing the proxy ds polynucleotide (positions 65-100). The base pairs with black background indicate the altered sites, which now make the dimer non-self-complementary. (The resulting modified oligos coincide with O−, and V+ of example 2). Upper sequence SEQ ID NO: 20; lower sequence SEQ ID NO: 21.

FIG. 5C. Mutagenizing primers used to modify the proxy ds polynucleotide to produce a ds polynucleotide which has the SOI. The underlined letters indicate the mutagenized bases. Upper sequence SEQ ID NO: 22; lower sequence SEQ ID NO: 23.

FIG. 6. Arrangement of the oligos, which were transferred from the library of example 1, on a 96-well plate to prepare them for annealing and hierarchical synthesis.

FIG. 7. Agarose gel electrophoresis (2%) showing the results of the hierarchical synthesis process. The top band is the one containing the 608 product. Left lane is a 50 bp ladder.

FIG. 8. Sequences of Example 4.

DETAILED DESCRIPTION OF THE INVENTION

Specific terms as used throughout the specification have the following meaning.

As used herein, the terms "a", "an" and "the" are used herein to refer to one or more than one, i.e. to at least one.

The term "sequence of interest" or "SOI" refers to the desired nucleotide or base pair sequence of the ds polynucleotide which is to be produced by the method provided herein.

The term "target double stranded (ds) polynucleotide" refers to a polynucleotide having a predefined sequence, which is produced by the synthesis method provided herein. Specifically, said target double stranded polynucleotide characterized by a sequence which is identical and/or corresponding to a SOI. If the target ds polynucleotide sequence has a sequence which is less than 100% identical to a SOI, the target ds polynucleotide is understood as a proxy ds polynucleotide that can be further modified to produce a ds polynucleotide that has a sequence which is identical and/or corresponding to the SOI.

The term "proxy double stranded (ds) polynucleotide" refers to a target double stranded (ds) polynucleotide whose sequence is less than 100% identical and at least 90%, preferably 95% identical to the nucleotide sequence of a SOI. In order to produce a ds polynucleotide having a sequence identical and/or corresponding to the SOI, and which is difficult to synthesize because its sequence may be prone to unambiguous assembly or runaway reactions, a proxy double stranded (ds) polynucleotide may be synthesized first. The sequence of the proxy double stranded polynucleotide is designed to avoid palindromic sequences, runaway reactions and unambiguous assembly and/or to facilitate hierarchical assembly. Specifically, the sequence may be designed computationally. The synthesized proxy ds polynucleotide may then be further modified to produce a ds polynucleotide with a nucleotide sequence identical to the nucleotide sequence of the SOI. Specifically, said proxy ds polynucleotide is further modified by any of directed mutagenesis, endonucleases or exonucleases, and/or enzymatic modification, employing any of methyltransferases, kinases, CRISPR/Cas9, multiplex automated genome engineering (MAGE) using A-red recombination, conjugative assembly genome engineering (CAGE), the Argonaute protein (Ago) or a derivative thereof, zinc-finger nucleases (ZFNs), transcription activator-like effector nucleases (TALENs), meganucleases, tyrosine/serine site-specific recombinases (Tyr/Ser SSRs), hybridizing molecules, sulfurylases, recombinases, nucleases, DNA polymerases, RNA polymerases or TNases to obtain a ds polynucleotide which has a sequence that is identical and/or corresponding to the SOI.

The term "template" refers to a polynucleotide characterized by a certain sequence, or a polynucleotide sequence, which sequence can be used to synthesize and produce a target ds polynucleotide. If a template is used in a synthesis method provided herein, the so produced target ds polynucleotide has a sequence which is 100% identical to the template.

Specifically, said template is single stranded or double stranded. Such template can be a natural nucleotide sequence or an artificial, computationally designed nucleotide sequence that comprises the desired product. Such template can be identical to a SOI or less than 100% identical to a SOI, preferably less than 95% identical, but at least 80% identical.

Preferably, said template is generated computationally and comprises the sequence of the leading strand of the target ds polynucleotide and the reverse complement of the target polynucleotide, respectively. Typically, two templates are used in the synthesis method described herein, one template for each of the strands of the target ds polynucleotide. When computationally designing a template sequence, compatibility with the experimental strategy used for assembly is preferred.

The term "single stranded DNA oligonucleotide", also referred to as "ssDNA oligonucleotide" or simply "ss oligonucleotide" or "ss oligo", shall refer to an oligonucleotide which is a linear polymer of nucleotide monomers. Monomers making up oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, wobble base pairing, or the like. ssDNA oligonucleotides described herein typically range in size between 6 and 26, but may be longer. ssDNA oligonucleotides described herein may range in size between 6 and 220 nucleotides, e.g. between 27 and 200 nucleotides. Whenever an oligonucleotide is represented by a sequence of letters (upper or lower case), such as "ATGC," it will be understood that the nucleotides are in 5'→3' order from left to right and that "A" denotes deoxyadenosine, "T" denotes deoxythymidine, "G" denotes deoxyguanosine, and "C" denotes deoxycytidine. Besides conventional nucleotides (A, G, C, T), modified nucleotides e.g. K-2'-deoxyribose, P-2'-deoxyribose, 2'-deoxyinosine, 2'-deoxyxanthosine or nucleotides with nucleobase analogs may be used e.g., inosine, or 5-methylisocytosine, or 3-nitropyrrole, 5-nitroindole, pyrrolidine, 4-nitroimidazole, 4-nitropyrazole, 4-nitrobenzimidazole, 4-aminobenzimidazole, 5-nitroindazole, 3-nitroimidazole, 5-aminoindole, benzimidazole, 5-fluoroindole, indole, methylisocarbostyril, pyrrolopyrimidine 7-propynylisocarbostryril. The terminology and atom numbering conventions follow those disclosed in Strachan and Read, Human Molecular Genetics 2 (Wiley-Liss, New York, 1999). Usually oligonucleotides comprise the four natural nucleosides (e.g. deoxyadenosine, deoxycytidine, deoxyguanosine, deoxythymidine for DNA or their ribose counterparts for RNA) linked by phosphodiester or by peptidyl linkages or by phosphorothioate linkages; however, they may also comprise non-natural nucleotide analogs, e.g. including modified bases, sugars, or internucleosidic linkages.

In some embodiments, the single stranded oligonucleotide pools are produced using chemical synthesis methods, e.g. by synthesizing the oligonucleotide sequence from monomer-phosphoramidites, dimer-phosphoramidites (Neuner, Cortese, and Monaci 1998) or trimer-phosphoramidites (Sondek and Shortle 1992), mixture of monomer-phosphoramidites, mixture of dimer-phosphoramidites, mixture of trimer-phosphoramidites or their combination thereof.

In some embodiments, the oligonucleotides are produced and purified from naturally-occurring sources, or synthesized in vivo, within the cell undergoing in vivo mutagenesis using any of a variety of well-known enzymatic methods e.g. as described in Farzadfard et al. (2014). Specifically, enzymes that synthesize soft-randomized oligonucleotide pools include, but are not limited to low fidelity DNA polymerase proteins or low fidelity reverse transcriptase proteins which incorporate mismatching nucleotides during synthesis with high frequency. Alternatively, mismatching nucleotides are incorporated into the oligos with a higher frequency by the DNA polymerases or reverse transcriptases due to the presence of chemical substances, which are well-known to those skilled in the art.

The term "base pair" or "bp", (used as abbreviation, singular or plural) also "bps" (in plural), refers to any of the pairs of nucleotides connecting the complementary strands of a molecule of DNA or RNA and consisting of a purine linked to a pyrimidine by hydrogen bonds. The pairs are adenine and thymine in DNA, adenine and uracil in RNA, and guanine and cytosine in both DNA and RNA.

The term "pairs of matching oligonucleotides" refers to two or more complimentary oligonucleotides. By "complementary" it is meant that the nucleotide sequences of similar regions of two single stranded nucleic acids or overhang parts of one or more ds nucleic acids, have a nucleotide base composition that allow the single-stranded regions to anneal together in a stable, double-stranded hydrogen-bonded region under stringent annealing or amplification conditions, such annealing is also referred to as "hybridization". When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotide sequences are 100% complementary. Besides conventional bases (A, G, C, T), analogs e.g., inosine and 2'-deoxyinosine and their derivatives (e.g. 7'-deaza-2'-deoxyinosine, 2'-deaza-2'-deoxyinosine), azole- (e.g. benzimidazole, indole, 5-fluoroindole) or nitroazole analogues (e.g. 3-nitropyrrol, 5-nitroindol, 5-nitroimidazole, 4-nitropyrazole, 4-nitrobenzimidazole) and their derivatives, acyclic sugar analogues (e.g. those drived from hypoxanthine- or indazole derivatives, 3-nitroimidazole, or imidazole-4,5-dicarboxamide), 5'-triphosphates of universal base analogues (e.g. derived from indole derivatives), isocarbostyril and other hydrophobic analogues, and any of its derivatives (e.g. methylisocarbostyril, 7-propynylisocarbostyril), hydrogen bonding universal base analogues (e.g. pyrrolopyrimidin), and other chemically modified bases (such as diaminopurine, 5-methylcytosine, isoguanine, 5-methyl-isocytosine, K-2'-deoxyribose, P-2'-deoxyribose) can have different base-pairing preferences and can pair with more than one natural nucleobase with similar stringency/probability. In certain cases, the monomers are linked by phosphodiester or by peptidyl linkages or by phosphorothioate linkages.

The term "double stranded DNA oligonucleotide", also referred to as "dsDNA oligonucleotide" or simply "ds oligonucleotide" or "ds oligo", shall refer to an oligonucleotide which is a linear polymer of nucleotide dimers. Dimers making up oligonucleotides are two complementary nucleotides bound by way of a regular pattern of monomer-to-monomer interactions, such as Watson-Crick type of base pairing, base stacking, Hoogsteen or reverse Hoogsteen types of base pairing, wobble base pairing, or the like. dsDNA oligonucleotides described herein typically range in size between 6 and 26 base pairs (bp), but may be longer. dsDNA oligonucleotides described herein may range in size between 6 and 200 base pairs, e.g. between 27 and 200 base pairs. Whenever an oligonucleotide is represented by a sequence of letters (upper or lower case), such as "ATGC," it will be understood that the nucleotides are in 5'→3' order from left to right and that "A" denotes deoxyadenosine, "T" denotes deoxythymidine, "G" denotes deoxyguanosine, and "C" denotes deoxycytidine. Besides conventional nucleotides (A, G, C, T), modified nucleotides e.g. K-2'-deoxyribose, P-2'-deoxyribose, 2'-deoxyinosine, 2'-deoxyxanthosine or nucleotides with nucleobase analogs may be used e.g., inosine, or 5-methylisocytosine, or 3-nitropyrrole, 5-nitroindole, pyrrolidine, 4-nitroimidazole, 4-nitropyrazole, 4-nitrobenzimidazole, 4-aminobenzimidazole, 5-nitroindazole, 3-nitroimidazole, 5-aminoindole, benzimidazole, 5-fluoroindole, indole, methylisocarbostyril, pyrrolopyrimidine 7-propynylisocarbostryril. The terminology and atom numbering conventions follow those disclosed in Strachan and Read, Human Molecular Genetics 2 (Wiley-Liss, New York, 1999). Usually oligonucleotides comprise the four natural nucleosides (e.g. deoxyadenosine, deoxycytidine, deoxyguanosine, deoxythymidine for DNA or their ribose counterparts for RNA) linked by phosphodiester or by peptidyl linkages or by phosphorothioate linkages; however, they may also comprise non-natural nucleotide analogs, e.g. including modified bases, sugars, or internucleosidic linkages.

The simplest DNA end of a double stranded molecule is called a blunt end. In a blunt-ended molecule, both strands terminate in a base pair. Non-blunt ends are created by various overhangs. The term "overhang" as used herein refers to a stretch of unpaired nucleotides at one or both ends of a ds oligo or polynucleotide molecule. These unpaired nucleotides can be in either strand, creating either 3' or 5' overhangs. The simplest case of an overhang is a single nucleotide. An overhang may comprise or consist of any one of 1, 2, 3, 4, 5, 6, 7, 8, 9, 10, 11 or 12 nucleotides, or at least any one of 1, 2, 3, 4, 5, 6, 7, 8, 9, 10, 11 or 12 nucleotides. An overhang is typically not more than half of a ds oligo length. For example, if said ds oligo is 6 nucleotides long, the overhang is not more than 3 nucleotides long, meaning the overhang can also be 1 or 2 nucleotides long. According to another example, if said ds oligo is 24 nucleotides long, the overhang is not more than 12 nucleotides long, meaning it can also be 1, 2, 3, 4, 5, 6, 7, 8, 9, 10 or 11 nucleotides long.

The term "library" as used herein shall refer to a collection of library members which are nucleic acid fragments (e.g. an oligonucleotide library) and which comprises at least 10.000 pairs of matching oligonucleotides. The library members can be single stranded oligonucleotides or double stranded oligonucleotides. The library members share common features (such as conferred by genomic sequences), but differ in at least one base pair, nucleotide, mutation and/or phenotype. A library typically contains library members which are diverse, besides those that have common features. One particular type of library is a library of randomized mutants of oligonucleotides, generated by random mutagenesis. Another specific example would be a rationally designed (or synthetic) library, e.g. a library which comprises specifically engineered DNA fragments or oligonucleotides. The library described herein comprises library members suitably composed of oligonucleotides of varying lengths and different sequences, wherein the oligonucleotides may correspond to a certain region of DNA or may even span the entire genetic space. Exemplary, the library may comprise a diversity of oligos necessary to possibly synthesize any and all naturally occurring polynucleotides of the human chromosomal genome or mitochondrial genome. In a further example said diversity may cover any and all naturally occurring polynucleotides of eukaryotic species other than human, such as e.g. mouse, rat, rabbit, pig, sheep, plants, funghi or yeast. In yet another example said diversity may cover any and all naturally occurring polynucleotides of prokaryotes, such as e.g. achaeans or bacteria.

The library provided herein, specifically comprises at least 10.000 pairs of matching oligonucleotides which are single stranded oligonucleotides, specifically they are ss oligos of varying lengths, comprising partially or fully complementary sequences. Said pairs of matching oligos may be present in the library as ss oligos in separate containments or two or more complementary ss oligos may be contained in one containment where they may anneal and form ds oligos. The nucleotide sequences of a pair of matching ss oligos may be complementary in at least 1, 2 or 3 nucleotides, preferably at least 4 or more nucleotides, such that a matching pair can form a new ds polynucleotide molecule by hybridization of the ss oligo sequences, preferably wherein the ss oligos hybridize in part, thereby obtaining a ds polynucleotide with an overhang.

The library preferably comprises oligonucleotides which are artificially or chemically synthesized, or chemically modified (e.g. including peptidyl nucleic acids or phosphorothioate bond) oligonucleotides synthesized by suitable methods well-known in the art. The oligonucleotides comprised in the library can also be generated by enzymatic digestion of naturally occurring DNAs. The members of said olignucleotide library described herein are specifically characterized by different sequences, mutations or nucleobase or nucleotide alterations, e.g. a substitution, or insertion or deletion of one or more subsequent nucleotides. Typically, the library members differ in at least one or more point mutation. Specifically, in some embodiments, the variation covers every possible naturally-occurring nucleobase residue at a certain position. If the mutants are produced by mutagenesis of a parent oligonucleotide, a variety of sequence variations of the parent oligonucleotide is produced.

The diversity of the library described herein may further comprise library members which are phosphorylated, methylated, biotinylated or which are linked to fluorophores or quenchers. As described herein, library members may comprise one or more additional phosphoryl groups.

Methylation of library members, the addition of a methyl group to a DNA molecule, preferably to cysteine or adenine, is performed according to suitable DNA methylation methods well-known in the art.

As used herein, biotinylation refers to a method of covalently attaching one or more biotin molecules to a nucleic acid, such as ss oligos or ds oligos. The library members described herein may be biotinylated by suitable methods well-known in the art; preferably it is a method of chemical biotinylation. Oligonucleotides can be readily biotinylated in the course of oligonucleotide synthesis by phosphoramidite methods well-known in the art, which use biotin phosphoramidite.

Members of the library described herein may be conjugated to a fluorophore by suitable chemical and enzymatic methods well-known in the art. Exemplary methods used for the fluorescent labeling of nucleic acids may employ a method for enzymatic labeling of DNA with fluorescent dyes e.g., using a Thermo Fisher's ARES DNA labeling kit, which employ a two-step method for enzymatic labeling of DNA with fluorescent dyes. Further exemplary methods may employ a chemical method for labeling nucleic acids without enzymatic incorporation of labeled nucleotides e.g., using a ULYSIS Nucleic Acid Labeling Kit. Further exemplary methods may employ chemical labeling of amine-terminated oligonucleotides to prepare singly labeled fluorescent oligonucleotide conjugates e.g., using an Alexa Fluor Oligonucleotide Amine Labeling Kit. Further exemplary methods may employ DNA arrays/microarrays and other hybridization techniques.

Library members may be linked to one or more quenchers, e.g., substances that absorb excitation energy from a fluorophore, by suitable methods well-known in the art. Examples of quenchers include but are not limited to Dabsyl (dimethylaminoazobenzenesulfonic acid), Black Hole Quenchers, Qxl quenchers, Iowa black FQ, Iowa black RQ and IRDye QC-1.

The term "point mutation" or nucleobase alterations as used herein shall refer to a mutation event altering a nucleic acid or amino acid sequence at a certain location, such as by introducing or exchanging single nucleobases or amino acids or introducing gaps. A point mutation or nucleobase alteration may involve a change in one or more single or adjacent or consecutive nucleobases or amino acid residues in a sequence. In a library comprising a repertoire of mutants covering a limited diversity, the frequency of point mutations in a sequence is limited, such that the mutants share at least a certain sequence identity to a parent (or reference) sequence, which is e.g. at least any of 80%, 90%, 95%, 96%, 97%, 98%, or 99%.

"Percent (%) nucleotide sequence identity" with respect to the nucleotide sequences described herein is defined as the percentage of nucleotides in a candidate sequence that are identical with the nucleotides in the specific nucleotide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

The term "diversity" as used herein, refers to a degree of versatility characterizing the library provided herein. Specifically, said diversity comprises single and double stranded oligos of different lengths and different sequences. For example, the library may comprise all possible sequence variations of 8 nucleobase long ss oligos (herein referred to as octamers), which are 65.536 different ss oligos of 8 nucleobases length, and in addition other ss oligos or ds oligos of different lengths, which are commonly comprised in target sequences and are thus required more often to build any given sequence. Including commonly used single or double stranded oligos into the library's diversity decreases synthesis cost and increases time efficiency.

Specifically, said diversity may cover an entire genome, for example the human genome. Specifically, said diversity may cover the entire genetic space. Specifically, said diversity may cover a genome or the entire genetic space multiple times in multiple ways. For example by encompassing all possible hexamer, heptamer and/or octamer sequence combinations. For example, said library may also encompass all or selected 9-mers and 10-mers or of any up to 26-mers.

According to a specific example, the diversity within a pool of oligonucleotides described herein is characterized as follows: the diversity may be determined by the number of mutations within the oligonucleotide sequence. For example, in a single oligonucleotide with a length of 16 nucleotides, the theoretical number of possible single nucleotide changes is 16×3=48 with the four naturally occurring DNA, A, T, G or C nucleotides. For two single nucleotide changes with the four naturally occurring DNA, A, T, G or C nucleotides per oligonucleotide (double mutants) the number of possible sequences is 6.408. For three single nucleotide changes per oligonucleotide (triple mutants) this number is 563.904. For quadruple mutations this number is 36.794.736. These numbers can further increase by incorporating non-natural nucleobases within the oligonucleotide sequence.

Exemplary methods for sequencing-based screening of oligonucleotides within a library are the following: SNP genotyping methods, including hybridization-based methods (e.g. molecular beacons, SNP microarrays, restriction fragment length polymorphism, PCR-based methods, including Allele-specific PCR, primer extension-, 5'-nuclease or Oligonucleotide Ligation Assay, Single strand conformation polymorphism, Temperature gradient gel electrophoresis, Denaturing high performance liquid chromatography, High-resolution Melting of the entire amplicon (HRM), SNPlex and surveyor nuclease assay; Sequencing based mutation analysis, including capillary sequencing or high-throughput sequencing of an entire PCR amplicon of the PTR (amplicon sequencing). Such such high-throughput (HT) amplicon sequencing methods include, but are not restricted to polony sequencing, pyrosequencing, Illumina (Solexa) sequencing, SOLiD sequencing, semiconductor sequencing, DNA nanoball sequencing, Heliscope single molecule sequencing, Single molecule real time (SMRT) sequencing, Nanopore DNA sequencing, tunnelling currents DNA sequencing, sequencing by hybridization, sequencing with mass spectrometry, Microfluidic Sanger sequencing, Microscopy-based sequencing, RNAP sequencing.

Each library member may be individually characterized and marked by a selectable marker or a DNA sequence tag or barcode, to facilitate the selection of a library member in the library or the identification of a library member in the library. Alternatively, the genetic mutation may be determined directly by a suitable determination method, e.g. high-throughput sequencing, capillary sequencing or employing specific probes hybridizing with a predefined sequence, to select the corresponding oligonucleotide.

It may be desirable to locate the library members in separate containers, to obtain a library of oligonucleotides in containers. According to a specific embodiment, the library is provided in an array, e.g. a DNA biochip, wherein the array comprises a series of spots on a solid carrier.

The term "mutagenesis" as used herein refers to a process of altering the sequence of an oligonucleotide or a polynucleotide. Specifically, site-directed mutagenesis refers to a method for creating a specific mutation in a known nucleotide sequence. This mutation is a specific, targeted change and may comprise single or multiple nucleotide insertions, deletions or substitutions. This task may be performed by restriction enzymes, specifically endonucleases and/or exonucleases. Endonucleases cleave the phosphodiester bonds in the middle of an oligonucleotide or a polynucleotide, whereas exonucleases cleave the phosphodiester bonds at the 5' or 3' end of an oligonucleotide or a polynucleotide.

The term "algorithm" as used herein refers to a self-contained sequence of actions to be performed. An algorithm is an effective method that can be expressed within a finite amount of space and time and in a well-defined formal language for calculating a function. Starting from an initial state and initial input the instructions describe a computation that, when executed, proceeds through a finite number of well-defined successive states, eventually producing "output" and terminating at a final ending state. The transition from one state to the next is necessarily deterministic.

The term "workflow" or "assembly workflow" refers to the optimal number of oligo subsets and their sequence of assembly into the target ds polynucleotide. In the method provided herein, the sequence of a template may be divided into sub-sequences, corresponding to subsets of oligos, avoiding particular nucleotide synthesis problems, such as palindromic sequences, runaway reactions and unambiguous assembly. In particular, such division into shorter oligonucleotides may be very efficient to shorten the assembly process and to avoid the need of separating unwanted reaction products. Specifically, ligation of subsets of oligos yields intermediate reaction products, also called intermediates, and assembly of intermediate reaction products ultimately yields the target ds polynucleotide. Preferably, additional criteria to those listed above may be used for selecting subsets of oligos. Such additional criteria include, but are not limited to, minimization of the size of the subset of oligos employed in any single ligation reaction (for example to avoid mismatch ligations), minimizing the difference in annealing temperature of members of a subset of oligonucleotide precursors, minimizing the difference in annealing temperatures of the overhangs of different double stranded subunits, whether to employ frame-shifting adaptors or single stranded oligo linkers and whether to minimize the degree of cross-hybridization among the hybrid forming portions of different oligos that make up a subset.

The number of oligos in a subset may vary. Preferably, the size of a subset is in the range of from 1 to 100, or from 2 to 100, more preferably in the range of from 1 to 50, or from 2 to 50 and still more preferably in the range of from 1 to 10, or from 2 to 10.

In a subset, wherein the degree of cross-hybridization has been minimized, a duplex or triplex consisting of a subunit of the set and the complement of any other subunit of the set contains at least one mismatch. In other words, the sequences of the oligos of such a subset differ from the sequences of every other oligo of the subset by at least one nucleotide, and more preferably, by at least two oligonucleotides. The number of oligonucleotide tags available in a particular embodiment depends on the number of subunits per tag and on the length of the subunit.

Single stranded oligo linkers having a sequence complimentary to the combined overhangs connect adjacent oligos in the target polynucleotide. Linkers may e.g. comprise 6 bases which connect two adjacent oligonucleotides each with a 3 base long overhang, one on the 3' end and the other on the 5' end, respectively.

In one specific embodiment of the invention the process of determining the assembly workflow is carried out by an algorithm. Candidate divisions of the sequence of the template are systematically examined to find the optimal number and assembly sequence of subsets to divide it into for synthesis in accordance with the method provided herein. Initially the entire template sequence is taken as a single subset, after which smaller and smaller subsets are formed with increasing numbers of candidate oligos in decreasing size until a partitioning is found that fulfills the subset criteria listed above.

The term "assembly" or "assemble" refers to the formation of an oligonucleotide or polynucleotide by linking and/or hybridizing single stranded and/or double stranded oligos. Specifically, said assembly is by any method of hybridizing ss nucleotide sequences, and/or a ligation reaction which is an enzymatic and/or chemical reaction. Preferably, said assembly is by an in vitro ligation method.

Assembly of the target ds polynucleotide can either be directly by hybridizing matching ss oligos, overhangs of ds oligos, or indirectly by hybridizing one or more suitable ss oligo linkers, wherein a ss oligo linker is contained in the library, and selected and transferred from the library to assemble any of said first, second or further reaction products.

For direct assembly oligonucleotide sequences are joined together by their single stranded oligo parts or overlaps (i.e. the overlapping parts or overhangs), such that the overlaps are included in the continuous sequence only once. Upon aligning two oligonucleotide sequences with an overlap, a continuous sequence is formed which has a length that is the length of both individual oligonucleotides taken together, minus the length of the overlap. Consequently, a continuous sequence is obtained which comprises a segment of each of the aligned oligonucleotides.

For indirect assembly, the target ds polynucleotide or any of said first, second or further reaction products are formed upon aligning ss oligos and joining them through single stranded linkers. For example, two oligonucleotides, each of e.g. 10 bases length, may be joined by an ss oligo linker of e.g. 6 bases length, such that 3 bases of the 3' terminal end of the first oligonucleotide align with the 3 bases of the 5' end of the ss linker and that 3 bases of the 5' end of the second oligonucleotide align with the 3 bases of the 3' end of the ss linker.

The terms "first, second or further reaction products" refer to the products of the ligation reactions performed in one or more reaction containments. In a first step, at least a first pair of matching oligonucleotides is transferred from the library into the first reaction containment using a liquid handler and the matching oligonucleotides are assembled in a ligation reaction thereby forming the first reaction product. Specifically, said first, second and further reaction products each comprise at least one overhang. Such overhang of a reaction product allows further assembly with another matching oligonucleotide in the direction of the overhang, e.g. to produce a new reaction product with an overhang, if the matching oligonucleotide included a first part that hybridizes with the overhang of said reaction product, and further included a second part that creates another overhang of the new reaction product. Alternatively, if the matching oligonucleotide only consisted of a part that hybridizes with the overhang over the full length of the overhang, such as to cover all nucleotides of the overhang, a blunt end can be created.

In specific cases, a ds target double stranded (ds) polynucleotide is produced which has a blunt end on one or both termini. Such blunt ends are preferably produced by hybridizing any terminal overhang with a matching ss oligo and/or ds oligo that hybridizes with the full-length of such overhang, without creating a new overhang, thus, producing a blunt end.

In said first step one or multiple pairs of matching oligonucleotides and one or multiple ss oligo linkers are transferred into said first reaction containment using a liquid handler and assembling the matching oligonucleotides thereby obtaining first reaction products. Preferably, the number of matching pairs transferred into said first reaction containment is any one of 1, 2, 3, 4, 5, 6, 7, 8, 9, 10, 15, 20 or 25, preferably 4 and even more preferably 1, 2, or 3, and the number of ss oligo linkers transferred is any of 0, 1, 2, 3, 4, 5, 6, 7, 8, 9, 10, 15, 20 or 25, preferably 4 and even more preferably 1, 2 or 3.

In a second and further steps, at least a second and further pairs of matching oligonucleotides are transferred from the library into a second and further reaction containments, respectively, using a liquid handler and assembling the matching oligonucleotides thereby obtaining a second and further reaction products, respectively. In said second step one or multiple pairs of matching oligonucleotides and one or multiple ss oligo linkers are transferred into said second reaction containment. Preferably, the number of matching pairs transferred in said second step is any of 1, 2, 3, 4, 5, 6, 7, 8, 9, 10, 15, 20 or 25, preferably 4 and even more preferably 1, 2 or 3 and the number of ss oligo linkers transferred is any of 0, 1, 2, 3, 4, 5, 6, 7, 8, 9, 10, 15, 20 or 25, preferably 4 and even more preferably 1, 2 or 3. In said further step, one or multiple pairs of matching oligonucleotides and one or multiple ss oligo linkers are transferred into said further reaction containment. Preferably, the number of matching pairs transferred in said further step is any of 1, 2, 3, 4, 5, 6, 7, 8, 9, 10, 15, 20 or 25, preferably 4 and even more preferably 1, 2 or 3 and the number of ss oligo linkers transferred is any of 0, 1, 2, 3, 4, 5, 6, 7, 8, 9, 10, 15, 20 or 25, preferably 4 and even more preferably 1, 2 or 3.

The number of steps and corresponding reaction products is unlimited. In order to synthesize large target ds polynucleotides steps a series of reaction products may need to be produced for assembly into the target polynucleotide, e.g at least 5, 10, 20, 50, 100, 500, 1.000, 5.000 or more may be necessary.

The terms "hybridize," "hybridization," "hybridizing," "anneal," and "annealing," as used herein, generally refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of a PCR, or the enzymatic cleavage of a polynucleotide by a ribozyme.

As used herein, the term "ligation" is intended to mean the process during which two nucleic acid sequences anneal to one another with intermolecular chemical bonds (e.g. hydrogen bonds) so as to form a double strand under appropriate conditions.

Ligation products, herein also referred to as reaction products, can be formed from both double stranded nucleic acids and single stranded nucleic acids. Double-stranded nucleic acids can be ligated by "sticky end" ligation or "blunt end" ligation. In sticky end ligation, staggered ends comprising terminal overhangs can hybridize to a ligation partner. In blunt end ligation, terminal overhangs are not present and successful ligation depends on transient associations of 5' ends and 3' ends. Blunt end ligations in general are less efficient than sticky end ligations, and various optimizations, such as adjusting concentrations, incubation times, and temperatures, can be applied to improve efficiencies. Single-stranded polynucleotides can also be ligated.

The ligation efficiency between two complementary sequences or sufficiently complementary sequences depends on the operating conditions that are used, and in particular the stringency. The stringency may be understood to denote the degree of homology; the higher the stringency, the higher percent homology between the sequences. The stringency may be defined in particular by the base composition of the two nucleic sequences, and/or by the degree of mismatching between these two nucleic sequences. By varying the conditions, e.g. salt concentration and temperature, a given nucleic acid sequence may be allowed to ligate only with its exact complement (high stringency) or with any somewhat related sequences (low stringency). Increasing the temperature or decreasing the salt concentration may tend to increase the selectivity of a ligation reaction.

The ligation reaction is performed by an enzyme, specifically a DNA ligase enzyme. The DNA ligase catalyzes the formation of covalent phosphodiester linkages, which permanently join the nucleotides together. In addition, T4 DNA ligase can also ligate ssDNA if no dsDNA templates are present, although this is generally a slow reaction. Non-limiting examples of enzymes that can be used for ligation reactions are ATP-dependent double-stranded polynucleotide ligases, NAD+ dependent DNA or RNA ligases, and single-strand polynucleotide ligases. Non-limiting examples of ligases are *Escherichia coli* DNA ligase, *Thermus filiformis* DNA ligase, *Thermus thermophilus* DNA ligase, *Thermus scotoductus* DNA ligase (I and II), CircLigase™ (Epicentre; Madison, Wis.), T3 DNA ligase, T4 DNA ligase, T4 RNA ligase, T7 DNA ligase, Taq ligase, Ampligase (Epicentre® Technologies Corp.), VanC-type ligase, 9° N DNA Ligase, Tsp DNA ligase, DNA ligase I, DNA ligase III, DNA ligase IV, Sso7-T3 DNA ligase, Sso7-T4 DNA ligase, Sso7-T7 DNA ligase, Sso7-Taq DNA ligase, Sso7-*E. coli* DNA ligase, Sso7-Amp ligase DNA ligase, and thermostable ligases. Ligase enzymes may be wild-type, mutant isoforms, and genetically engineered variants. Ligation reactions can contain a buffer component, small molecule ligation enhancers, and other reaction components.

Preferably, the T4 DNA ligase is used in the ligation reaction. In the method provided herein the ligation reaction is performed under high-fidelity conditions that block side reactions and minimize mismatches.

Assembly into intermediate reaction products or into the target polynucleotide may be carried out using suitable ligation buffer solutions. The ligation buffer solution is e.g. an aqueous solution, typically in a nuclease free environment, at a pH that ensures the selected ligase will be active; typically, this is a pH of between about 7-9. Preferably, the pH is maintained by Tris-HCl at a concentration of between about 5 mM to 50 mM. The ligation buffer solution may include one or more nuclease inhibitors, usually calcium ion chelators, such as EDTA. Typically, EDTA is included at a concentration of between about 0.1 to 10 mM. The ligation buffer solution includes whatever cofactors are required for the selected ligase to be active. Usually, this is a divalent magnesium ion at a concentration of between about 0.2 mM to 20 mM, typically provided as a chloride salt. For T4 DNA ligase ATP is required as a cofactor. The ligase buffer solution may also include a reducing agent, such as dithiothreitol (DTT) or dithioerythritol (DTE), typically at a concentration of between about 0.1 mM to about 10 mM. Optionally, the ligase buffer may contain agents to reduce nonspecific binding of the oligonucleotides and polynucleotides. Exemplary agents include salmon sperm DNA, herring sperm DNA, serum albumin, Denhardt's solution, and the like. Preferably, ligation conditions are adjusted so that ligation will occur if the first and second oligonucleotides form perfectly matched duplexes with the bases of the contiguous complementary region of the target sequence. However, it is understood that it may be advantageous to permit non-pairing nucleotides on the 5' end of the first oligonucleotide and the 3' end of the second oligonucleotide in some embodiments to aid in detection or to reduce blunt-end ligation. Important parameters in the ligation reaction include temperature, salt concentration, presence or absence and concentration of denaturants such as formamide, concentration of the first and second oligonucleotides and type of ligase employed. Methods of selecting hybridization conditions for the reaction are known to those skilled in the art.

Preferably, ligation occurs under stringent hybridization conditions to ensure that only perfectly matched oligonucleotides hybridize. Typically, stringency is controlled by adjusting the temperature at which hybridization occurs while holding salt concentration at some constant value, e.g. 100 mM NaCl, or the equivalent. Other factors can be relevant, such as the particular sequence of the first and second oligonucleotides, the length of the first and second oligonucleotide and the heat lability of the ligase selected. Preferably, the ligation reaction is carried out at a temperature close to the melting temperature of the hybridized oligonucleotides in the ligation buffer. More preferably, the ligation reaction is carried out at a temperature within 10° C. of the melting temperature of the hybridized oligonucleotides in the ligation buffer solution. Most preferably, the ligation reaction is carried out at a temperature in the range of 0 to 5° C. below the melting temperature of the hybridized oligonucleotides in the ligation buffer solution.

Ligation may be followed by one or more amplification reactions. In some embodiments, the ligation products, or target polynucleotides are isolated or enriched prior to amplification. Isolation can be achieved by various suitable purification methods including affinity purification and gel electrophoresis. For example, ligation products, or target polynucleotides can be isolated by binding of a selective binding agent immobilized on a support to a tag attached to the capture probe. The support can then be used to separate or isolate the capture probe and any polynucleotide hybridized to the capture probe from the other contents of the sample reaction volume. The isolated polynucleotides can then be used for amplification and further sample preparation steps. In some embodiments, the capture probe is degraded or selectively removed prior to amplification of the circular target polynucleotides. Amplification of reaction products, or target polynucleotides can be achieved by various suitable amplification methods known to those skilled in the art.

The term "derivative" refers to an oligonucleotide or a polynucleotide differing from the original oligonucleotide or polynucleotide, but retaining essential properties thereof. Derivatives may e.g. be produced using a ds polynucleotide (e.g. DNA) as a starting material to engineer single stranded DNA, or complementary RNA molecule, to introduce one or more point mutations, or to bind heterologous moieties or tags by chemical and/or enzymatic means.

Generally, derivatives are overall closely similar, and, in many regions, identical to the original oligonucleotide or polynucleotide. As a practical matter, whether any particular nucleic acid molecule or polypeptide is at least 90%, 91%, 92%, 93%, 94%, 95%, 96%, 97%, 98%, 99%, or 100% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. BIosci. (1990) 6:237-245). In a sequence alignment the query and subject sequences are both DNA sequences. An RNA sequence can be compared by converting U's to T's. The result of said global sequence alignment is in percent identity. If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 impaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for.

The library of the present invention may comprise thousands of oligos necessary to cover the whole sequence space. Each of the oligonucleotide library members may be physically placed in a compartment. All compartments may be conveniently provided within one or more parts of a device, which together are provided as "array device". Such array device may be any one or more of a microtiter plate, microfluidic microplate, set of capillaries, microarray or a biochip, preferably a DNA or RNA biochip. Oligos may be conveniently transferred by automated means, e.g. either robotically or via dedicated fluids using, for example, an automated liquid handler, from such compartments into other compartments herein referred to as reaction compartments, i.e. from one vessel to another. In order to facilitate time efficient assembly of polynucleotides, hierarchies of reactions and respective vessels may be employed corresponding to frequency of use of oligonucleotide library members. The transfer to a new vessel involves the physical movement of a device that picks one or more molecules of an oligo from the respective location, or the pneumatic/hydraulic deposition though microfluidics. Due to the large number of oligos required to theoretically build any given sequence, most spatial distributions of library members in the library would incur into wasted time and resources due to scanning of the library and lengthy travel times of the liquid handler. However, by using a specific distribution of the library members, it can be ensured that that there is minimal movement according to a target sequence. One example is to store into micro-well plates where the first plate comprises the most common pair combinations of oligos, in decreasing order until the last micro-well plate which contains the least-frequently used library members.

Specifically, said separate library containments are spatially arranged in a two-dimensional order, wherein the individual compartments are located within a device at defined coordinates within the x- and y-axes. The order is specifically predefined by a parameter which primarily serves to shorten synthesis time. Preferably, said parameter is frequency of use, placing those oligos in close proximity to each other which frequently form a matching pair in DNA sequences, e.g. naturally occurring or commonly used in target ds polynucleotides or fragments thereof. Even more preferably, said separate library containments are spatially arranged in a three-dimensional order, wherein the individual compartments are located within a device at defined coordinates within the x-, y- and z-axes. The order is specifically determined by the frequency of use, placing those oligos in close proximity to each other which frequently form a matching pair in naturally occurring DNA sequences. Specifically, the spatial arrangement of library members may depend on any one of, or a multitude of the following parameter: frequency of use of the oligonucleotides, frequency of occurrence of the oligonucleotides in natural DNA sequences, frequency of occurrence of the oligonucleotides in a set of designed DNA sequences, minimization of handling or access time by the microfluidic device, minimization of operational cost or of amount consumables by the microfluidic device.

In a specific example, said separate library containments are micro-well plates, arranged as stacked plates, optionally barcode labelled, and accessible by an automated microdroplet handler. Library members may be conveniently stored in said stacked micro-well plates, wherein the order and stacking is according to decreasing frequency of use.

As used herein the terms "liquid handler", "automated handler" or "microdroplet handler" refer to any device used in a method of liquid handling, preferably, automated liquid handling, preferably a device as used in sensor-integrated robotic systems. As low-volume dispensing becomes increasingly common in life science, microsyringes have emerged which have a high level of precision with hermetic seals. Some manual or electronic holders are designed to precisely control the piston displacement to ensure the accuracy of the dispensed volume. Besides the syringe, a pipette is another popular tool for liquid handling. The dispensed volume can be at the micro- or sub-microliter level. Multichannel pipettes are recommended for multirouting pipetting at one time. There are both fixed- and adjustable-volume pipettes on the market. The former is more accurate and precise, whereas the latter has a larger scope of applications because the operator can choose different volumes according to need. Besides, high throughput has become critically important in life science research. One of the representative applications is microarray printing. This technology creates an array of biosample spots each at the nanoliter scale to enable the analysis of large numbers of experiments in parallel with only tiny quantities of samples. The process of spotting thousands of biosamples is almost an impossible task with a handheld dispensing tool, making robotic liquid handling an important aspect.

Robotic workstations have multiple advantages over manual liquid handling since robots can work without fatigue, increase the throughput, perform consistently, and ensure accuracy and precision. According to the requirements for the platform with integration and multifunction, there are still more complex systems in which the liquid-handling task is only one part of the function. The generic architecture of liquid-handling may be built up as follows. First, the control center controls a robot that moves between the dispensing part and the washing station of the robotic workstation. The washing station is used to clean the dispensing head for lengthening its life and for ensuring the safety of the sample. Liquid samples are expelled from the dispensing head and deposited on the substrates for further processing. Sensors are incorporated to monitor the status of the dispensing part such that feedback control can be performed by the control center. Sensors are not always installed on all the workstations but are more and more used to construct the feedback loop for delivering a better performance.

The term "capillaries" refers to any of glass capillaries, microfluidic capillaries and autonomous microfluidic capillary systems. Capillary microfluidics are important tools in many different fields. Due to their axisymmetric flow and ability to withstand organic solvents, when compared with their lithographically fabricated polydimethylsiloxane (PDMS) counterparts, glass capillary devices possess advantages for microfluidic applications. In particular, a circular tube is inserted into a square outer flow channel, which greatly simplifies alignment and centering of these devices. These devices can produce small and large droplets, ranging from 10 to multiple hundreds in μm size.

The term "microtiter plate" refers to any of well plates, multi-well plates or micro-well plates. These plates are commonly manufactured in a 2:3 rectangular mix with 96, 384, or 1536 wells, although other cavity configurations are available. Some of the other sizes, far less common, available are 6, 24, 3456, and 9600 wells. The wells of the microplate typically hold between tens of nanoliters to several milliliters of liquid.

The term "microarray" refers to a supporting material (such as a glass or plastic slide) onto which numerous molecules or fragments usually of DNA or protein are attached in a regular pattern. More specifically, it refers to microscope slides that are printed with thousands of tiny spots in defined positions, wherein said spots are capable of binding DNA or RNA. Such slides are often also referred to as biochips, DNA chips, RNA chips or gene chips. Such microarrays can bind DNA or RNA in a covalent or non-covalent manner and can thus serve as array devices in which oligos are stored in pre-defined locations, i.e. spots.

"Microfluidic devices" enable the manipulation of discrete fluid packets in the form of microdroplets that provide numerous benefits for conducting biological and chemical assays. Among these benefits are a large reduction in the volume of reagent required for assays, the size of sample required, and the size of the equipment itself. Such technology also enhances the speed of biological and chemical assays by reducing the volumes over which processes such as heating, diffusion, and convective mixing occur. Once the droplets are generated, carefully designed droplet operations allow for the multiplexing of a large number of droplets to enable large-scale complex biological and chemical assays.

The term "microfluidic microplate" refers to a combination of microfluidic technology with standard SBS-configured 96-well microplate architecture, in the form of microfluidic microplate technology. A microfluidic microplate allows for the improvement of essential workflows, conservation of samples and reagents, improved reaction kinetics, and the ability to improve the sensitivity of the assay by multiple analyte loading (Kai et al., 2012).

The term "methyltransferase" as used herein, can refer to any of DNA methyltransferase, RNA methyltransferase, protein methyltransferase and histone methyltransferase. Methyltransferases can be further subdivided into class I, all of which contain a Rossman fold for binding S-Adenosyl methionine (SAM) and class II methyltransferases, containing a SET domain, which are exemplified by SET domain histone methyltransferases, and class III methyltransferases, which are membrane associated.

The term "CRISPR/Cas9" refers to a gene editing method well known to those skilled in the art, as well as modifications thereof. Such modifications include, but are not limited to, fusion of a nuclease-dead Cas9 (dCas9) to cytidine deaminase, enabling site-specific conversion of cytidine to uracil and mutations to the Cas9 protein, which generate versions of the Cas9 protein that only create single-strand DNA cuts (nicks).

The terms "multiplex automated genome engineering" or "MAGE" refer to a technique which generally includes introducing multiple nucleic acid sequences into one or more cells such that the entire cell culture approaches a state involving a set of changes to a genome or targeted region. The method can be used to generate one specific configuration of alleles or can be used for combinatorial exploration of designed alleles optionally including additional random, or non-designed, changes.

ssDNA-binding protein mediated recombination, homologous recombination and MAGE-based methods typically include introducing multiple oligonucleotides into a cell including the steps transforming or transfecting cells using transformation medium or transfection medium including oligonucleotides, replacing the transformation medium or transfection medium with growth medium, incubating the cell in the growth medium, and repeating the steps if necessary or desired until multiple nucleic acid mutations have been introduced into the nucleotide sequence of interest. Increasing the number of cycles of mutagenesis generally increases the diversity of mutations introduced.

MAGE particularly employs a highly efficient lambda phage red recombination system (the λ Red System) which is a process by which the genome of a cell is reprogrammed to perform desired functions via a form of accelerated, directed evolution. The λ Red System includes β, γ, and exo genes, whose products are called Beta, Gam, and Exo, respectively. Gam inhibits the host RecB,C,D exonuclease and the SbcC,D nuclease activities, so that exogenously added linear DNA is not degraded. The Exo protein is a dsDNA-dependent exonuclease that binds to the terminus of each strand while degrading the other strand in a 5' to 3' direction. Beta binds to the resulting ssDNA overhangs, ultimately pairing them with a complementary chromosomal DNA target. The λ Red System has been widely utilized for specific gene inactivation in *E. coli, Salmonella, Citrobacter* and *Shigella* species, and for introducing small biological tags or single genes into these chromosomes.

The term "conjugative assembly genome engineering" or "CAGE" refers to a precise method of genome assembly using conjugation to hierarchically combine distinct genotypes from multiple *E. coli* strains into a single chimeric genome. CAGE permits large-scale transfer of specified genomic regions between strains without constraints imposed by in vitro manipulations. Strains are assembled in a pairwise manner by establishing a donor strain that harbors conjugation machinery and a recipient strain that receives DNA from the donor. Within strain pairs, targeted placement of a conjugal origin of transfer and selectable markers in donor and recipient genomes enables the controlled transfer and selection of desired donor-recipient chimeric genomes. By design, selectable markers act as genomic anchor points, and they are recycled in subsequent rounds of hierarchical genome transfer.

"Ago" refers to the Argonaute protein which has shown to provide DNA-based DNA interference, where a single-stranded DNA guide could direct Ago-based cleavage of a plasmid DNA target. A key advantage is that, unlike CRISPR-Cas9, there is no requirement of a Protospacer adjacent motif (PAM).

Zinc-finger nucleases (ZFNs) and transcription activator-like effector nucleases (TALENs) recognize DNA target sites, ranging from 25 to 40 bp in size, in a sequence-specific manner through their DNA-binding domains and generate staggered double strand breaks through the action of FokI nuclease domains on opposite DNA strands.

"Meganucleases", also known as homing endonucleases, recognize a specific DNA sequence between 14 and 40 bp upon which they cut and induce a DSB. The efficiencies of meganucleases are reasonably high, and they only require a single custom biopolymer for each target site.

"Tyrosine/serine site-specific recombinases" or "Tyr/Ser SSRs", which typically recognize target sequences between 30 and 40 bp in length, were one of the earliest genome-engineering tools to enable homology-directed repair (HDR) in mammalian genomes. Briefly, the target site comprises three parts, a short DNA sequence flanked by two inverted repeats, and recombination can occur between a pair of target sites, where the DNA sequence between the target sites can be deleted, inverted or replaced. Notably, whereas Tyr SSRs utilize a mechanism of strand exchange without creating double strand breaks, Ser SSRs do create double strand breaks, but unlike simpler designer double-strand nucleases, SSRs require concerted cleavage and re-ligation with the donor DNA present.

The foregoing description will be more fully understood with reference to the following examples. Such examples are, however, merely representative of methods of practicing one or more embodiments of the present invention and should not be read as limiting the scope of invention.

EXAMPLES

In the following examples it is described how the library of oligos is produced, how it is handled and its contents and properties are verified. Furthermore, it is described how a polynucleotide is synthesized according to the method provided herein.

Example 1: Production of the Library 1.1 Determining the Spatial Structure of the Genetic Information A. First, all the sequences of oligonucleotides that are to be included in the library have to be listed. These sequences are pre-computed from an input set of sequences that cover all potentially desired targets. This information can come from a diversity of criteria, such as a subset of possible combinations (e.g. all heptamers, all octamers, etc.), predicted outcome of the digestion of a genome with a set of restriction enzymes or any other computational criterion.

In this example the Human mitochondrial genome (Gene Bank accession nr. J01415; Anderson et al., 1981), which has 16569 base pairs, served as basis for the library. Ideally, all reported sequences would be taken and processed in the same way as described below and in FIG. 1.

The reference genome sequence was partitioned into oligonucleotide dimers of lengths between 8 and 26 bp. Similarly, the reverse-complement was computed and it was partitioned into oligonucleotides of lengths between 8 and 26 nt. This resulted in a total of 2.070 oligos that can form ds structures with 4 nt overhangs (See FIG. 1). Next the same process was carried out repeatedly by shifting the sequence first 1, then 2, then 3, up to 15 nucleotides. As a result there were 2070×16=33.120 oligos in the library.

There are at least 16544 matching pairs in this database if we only count those that overlap by 4 bp. Generally speaking, variant sequences should be processed in a similar way, which increases the multiplicity in a non-linear way. For instance, a window of about 100 bp containing only 16 polymorphic sites adds over 400 oligos and almost 20.000 matching pairs (FIG. 1). The combinatorics imply that when considering more variable sites, the oligo library is populated in a non-polynomial fashion with the number of sequence variants that are considered in its design.

Some of the oligos were conserved across haplotypes and were allocated in the library as paired elements (FIG. 1B). The oligos spanning variable sites (and depending on the extent of the variability) were kept independently as ssDNA elements.

B. The 2-dimensional arrangement of the library was determined by sorting library members according to a preferred criterion. Here, 16-mers were sorted first by sequence shift and second according to their order of first occurrence in the sequence and by alternating conjugate pairs. When alternative oligos occurred for a given position they were sub-sorted according to the frequency of their occurrence. Oligos that are conserved across all input sequences were allocated with their conjugated pair in the same position.

Alternative criteria that reflect both the individual usage of an oligo and also the relative usage of its matching pairs could be lexicographically, length, adjacency of matching pairs, frequency, or any other arbitrary but known way.

C. Next, the first sequence was allocated into a 2-dimensional array corresponding to the position(s) in a 1536 micro-well plate where the actual oligo(s) were to be placed.

D. The subsequent oligos were added until the 1535 remaining wells were all occupied by oligos in an order reflecting the sorting preference of step B.

E. Step C was then repeated with the next 1536 oligos, and so forth until all 33.120 or more oligos were distributed in micro-well plates.

F. The information was stored digitally to keep track of the location of each oligo. At a later step this served two purposes: first, it functioned as a look-up table for easier access to oligos and, secondly, it allowed monitoring of usage and access frequency of every oligo in order to keep track of available volumes.

1.2. Synthesis of the Library

Once the sequence was properly structured the actual synthesis of each oligo was carried out. Physically, the library used to construct the Human mitochondrial genome consists of 27 1536-micro-well plates (Corning 1536 well plates, Sigma Aldrich Product Nr. CLS3726-50EA), made of polypropylene (polypropylene is preferred, however any material that minimizes DNA absorption to the surface can be used). Each of the plates was labeled and/or barcoded unambiguously for easy access and for content bookkeeping.

Each produced oligo was located in its predefined plate as determined above. In this example, the oligos were phosphorylated at the 5' end. Other applications might require treatment with other modifications such as di- or tri-phosphates, biotin, TEG or thiol modifiers, etc. at the 3', 5' or both ends, or methylations, etc. Oligos were kept in aqueous solution (nuclease free ddH20 or TRIS 10 mM pH 8.0 and 1 mM EDTA) at a volume of 10 μL per oligo per micro-well at a concentration of 200 μM (Sambrook and Russell, 2014).

The actual production of the library can be carried out with standard methods of molecular biology by digesting with nucleases naturally occurring DNA, chemically constructed with oligo-synthesizers, etc. followed by separation and purification with HPLC, capillary electrophoresis or other techniques. Because the synthesis and modification of oligonucleotides is standard, it can also be outsourced from many services. According to this example, the library was produced using automatic DNA synthesizers that implement iteratively the chemical reaction of deoxynucleoside phosphoramidites to covalently bond mononucleotides to a solid-phase-attached polynucleotide (Beaucage and Cartuthers, 1981).

The library was stored at −20° C. when not in use for short periods, or −80° C. for long term storage.

1.3 Usage of the Library

A. The library was thawed by placing the plates at 3° C. for at least 60 minutes and then kept on ice or on a cooler plate at a temperature between 3-5° C.

B. Each micro-well plate was vortexed for 30 seconds in an orbital mixer at 2500 rpm and spun down in a centrifuge for 1 min at 900 rpm.

C. Using a low-volume micro-droplet handler (TPP Lab Tech Mosquito X1) 100 nL (recommended range: 50-250 nL) were transferred to a fresh 384 micro-well plate (other capacities such as 96 or 1536, or surface can also be used) that contained 1.8 µL of a solution or solution droplet (recommended range is of 1-5 µL) where the oligos were combined and/or further reacted.

D. In the digital database the used volume of the respective micro-wells was annotated to ensure there was always enough of all required oligos for a further round of usage. Note that some liquid handlers provide accurate and real-time measurement of the used and remaining volumes in each accessed well. This function may aid a more accurate tracking.

E. Once the library had been used, it was returned to storage at −80° C.

1.4 Determining the Properties of the Library

The main properties defining a library of the present invention are i) defined lengths of the oligonucleotides, ii) single stranded and/or double-stranded with at least one overhang and iii) a certain number of oligos. The main properties of the library used in this example were i) lengths of oligonucleotides ranging from 8 to 26 nt, ii) presence of single stranded and double stranded oligos with at least one overhang and iii) at least 33.120 oligos are included in the library.

It is desirable to be able to verify that these properties hold for purposes of quality control.

I. Verifying the Length of the Oligonucleotides.

Using a micro-droplet handler aliquots of 5-10 nL of each micro-well were taken and pooled into a common solution. Alternatively, random aliquots were taken and pooled into 10 different pooled solutions in such a way that each oligo is in only one of the pools. The pool or pools were mixed by vortexing. A small aliquot of a few µL per pooled solution was run through capillary electrophoresis (Kemp, 1998). Alternatively, the samples can be analyzed on a 25% acrylamide gel, and compared with a standard ladder ranging from 6 to 24 bp of ssDNA.

II. Verifying the Structure of the Oligonucleotides Present in the Library.

ss oligos, ds oligos and ds oligos with ss overhangs were differentiated by comparing denatured but otherwise untreated samples of a given oligo with a sample treated with an exonuclease, such as *E. coli* Exonuclease I (e.g. Thermo Scientific Exonuclease I, product nr. EN0581). This enzyme digests ssDNA to mono-nucleotides and di-nucleotides, but leaves dsDNA intact (Lehman and Nussbaum, 1964). Therefore the untreated and treated samples gave one of the following results when inspected through capillary electrophoresis:

The untreated sample showed a single band within a range of 6-26 nt, and the treated sample showed no bands. This implied that the original sample consisted of ss DNA.

The untreated sample showed a single band within a range of 6-26 nt, and the treated sample showed the same band. This implied that the original sample consisted of ds DNA (with no overhangs).

The untreated sample showed two different bands, both within a range of 6-26 nt, and the treated sample showed a single band whose length coincided with the smallest band of the untreated sample. This implied that the original sample consisted of a dimer of DNA that has one overhang. The length of the overhang is the difference of the sizes of the two bands of the untreated sample, and the length of the ds part is that indicated on the treated sample.

The untreated sample showed a single band, within a range of 6-26 nt, and the treated sample showed a single band whose length was smaller than that of the untreated sample. This implied that the original sample consisted of a dimer of DNA that had two overhangs of equal size. The length of the overhangs is the difference of the sizes of the treated and untreated samples, and the length of the ds part is that indicated by the band of the treated sample.

The untreated sample showed two bands, both within a range of 6-26 nt, and the treated sample showed a single band whose length is smaller than both of the untreated samples. This implies that the original sample consisted of a dimer of DNA that had two overhangs of different sizes. The lengths of the overhangs are determined by the difference of the sizes of each band relative to the size given by the treated sample, and the length of the ds part is that indicated on the treated sample.

Other analytical techniques, such as HPLC can also reveal in their spectra the composition of an untreated sample, directly indicating the presence of a single species of DNA or of two of them, providing direct evidence of the nature of the oligonucleotides in one well of the library. Also, circular dichroism could be used to distinguish among single and double stranded DNA and even dsDNA with overhangs.

III. Verifying the Number of Oligonucleotides and Number of Matching Pairs.

A sample of 50-100 nL of the contents of each micro-well was pooled into a common solution annealed by heating at 95° C. for 3 minutes and allowed to cool down at least to room temperature or down to 16° C. The corresponding buffer necessary for ligation was added including necessary cofactors such as Mg+, ATP, etc. Enough ligase (e.g. T4 ligase, NEB, product nr. M0202) to catalyze the reaction (1 U per µL of reaction solution) was added. The reaction mix was incubated for an hour at room temperature or overnight at 16° C.

By hypothesis, if there are enough matching pairs, the ligase will covalently link them, resulting in DNA molecules of a range of lengths with random sequences. The distribution of lengths was resolved by using electrophoresis with Agarose 2-4% on TAE. Samples run together with a suitable ladder (on a separate lane; recommended 50 or 100 bp) showed a smear of DNA along the sample lane with no discrete bands. A narrow range of approximately 100-200 bp was isolated by cutting the gel guided by the ladder (Sambrook and Russell, 2014; Ch. 5). Following standard protocols for gel-extraction, the DNA from the excised agarose block was isolated (e.g. Zymoclean gel DNA recovery kit, Zymo research, product nr. D4001T). After purification, the sample was deep-sequenced in order to determine the different sequences in the pool (Bentley et al., 2008).

The following analysis was performed in order to estimate the number of oligos and of matching pairs. If the starting material for the reaction consists of DNAs between 6 and 26 nt, and the sequences are not highly repetitive it could be concluded that, in average, there are at least 2×N×100/26 oligos (N being the number of reported sequences), and up to 2×N×200/6 oligos and almost as many matching pairs. Further bioinformatic analyses were used to extract the sequences of the oligos, as follows. The first 6 nt of one of the sequences were taken, a search & match for this pattern in the complete sequence pool was performed, and the number of occurrences was annotated. This was repeated for 7 nt, then for 8 nt and so on until 26 nt. By using a statistical T-test, it was determined which number is significantly different from random occurrences. This distinctive pattern was stored in a list of putative oligos and all its occurrences were eliminated from the database. This procedure was repeated with the remaining sequences until only DNA sub-sequences between 6 and 26 nt, that cannot be further partitioned, and which are now added to the list of patterns, were left. The number of identified oligos was called M. Since these oligos were linked to at least one other oligo, it implied that, together with their partial complements in the opposite strand, consecutive oligos were part of matching pairs. Hence there were at least as many matching pairs as number of identified oligos, except for those at the termini. For instance there were on the order of M-N matching pairs. Statistical analysis and bootstrapping simulation was performed to determine whether the identified number can be expected to be a subsample of a larger set of at least 33.120 oligos.

Example 2: Synthesis of a Target DNA Molecule of 128 bp

In this example it was demonstrated how to synthesize a sequence of 128 bp by means of the method proposed herein. FIG. 2A shows the sequence of interest, which was termed DISCOVER, and was built from 16 matching pairs (FIG. 2B) that formed 8 ds oligos of 16 nt with 4 nt overhangs on each strand (see FIG. 2C) and 8 complementary sites. Each ds oligo is denoted by the letters D, I, S, C, O, V, E, R and their constituting leading and lagging strands by + and − superscripts, respectively. The oligos were part of the library generated in example 1. It has the following properties: all oligos were phosphorylated at the 5' end, they were provided at a concentration of 200 μM on nuclease free ddH20 and the used oligos were single-stranded and pure.

A. Preparing the Annealing Solutions.

In a reaction tube 252 μL on ddH20 with TRIS-HCl (50 mM), MgCl2 (10 mM), DTT (10 mM) and ATP (1 mM) were prepared. The pH was set to 7.5. Some commercial buffers are ready to mix in H20 such as New England Biolabs' Ligase Reaction Buffer, product nr B02025, and readily contain the ATP necessary for the ligase activity. Solution was mixed well by vortexing. 28 μL of this solution mix were dispensed into to 8 micro-wells in a 4×2 array. 1 μL of each oligo was transferred to a predefined micro-well of the plate and mixed well by pipetting:

D+ and D− to well A1
I+ and I− to well A2
S+ and S− to well A3
C+ and C− to well A4
O+ and O− to well B1
V+ and V− to well B2
E+ and E− to well B3
R+ and R− to well B4

B. Annealing.

The plate was sealed and incubated in a thermocycler for 5 min at 95° C. allowing the matching pairs of ss oligos to anneal. The temperature was then decreased to 16° C. with a ramp function that diminished the temperature by 1° C. per minute. Once finished the double stranded oligos were kept at 16° C.

C. Preparing the Ligation Solution.

The ligation solution was prepared on ice by mixing, in the following order, 13.3 μL of nuclease free ddH20, 2 μL of ligase buffer and 4 μL of ATP for a final concentration of 1 mM. The ligation solution was mixed well by vortexing and spun down. 0.7 μL of T4 Ligase (NEB, product nr. M0202) were added for a total of 1 unit per μL of final solution and mixed well by gently pipetting. The solution was kept on ice until needed. 2.5 μL of the ligation solution were transferred to each of the 8 micro-wells containing the ds oligos of B and mixed by pipetting. Afterwards the plate was sealed again.

D. Ligation Rounds.

For the first round of ligation the following wells were merged as follows: D+I, S+C, O+V, E+R. This was achieved by transferring the contents of one well into the other (transferring the contents of both wells into a new well is also possible). A scheme was used where the leftmost contents are transferred to the rightmost (FIG. 3A). The ligation reaction mix was incubated at 16° C. for at least one hour. This process was repeated by merging the wells DI+SC and OV+ER (FIG. 3B) and again each was incubated for one hour. For the final ligation round the wells DISC+OVER were merged and incubated for another hour (FIG. 3C). The final volume containing the 128 bp product was 140 μL.

E. Purification.

An agarose gel 2% (1 mg agarose in 50 mL TAE supplied with 5 μL of SYBR Safe DNA stain) with a comb of 11 wells was prepared. 4.5 μL of 50 bp ladder (New England Biolabs product nr. N3236 or Invitrogen product nr. 10416014) was added on the first lane and the 140 μL of solution obtained under step D were distributed across the remaining wells. The gel was run at 85 V, 200 mA and 12 Watt for 50 minutes. After the electrophoresis was completed, the gel was placed over a UV trans-illuminator and the bands of the gel that correspond to the 128 bp fragment were excised. Purification of these bands can be performed with commercial Kits for said purpose (e.g. Zymoclean, see previous example), or following any standard protocol for this purpose.

F. Amplification.

To further increase the amount of product, the product obtained under step D was amplified by PCR (Sambrook and Russell, 2014; Chapter 8). The starting 16 nt D− and R+ were used as primers for said amplification. After amplification, the construct was freed from enzymes and primers and separated into two aliquots, one for further use, which was labeled and stored at −20° C. and the other one was used to sequence-verify the construct.

FIG. 4 depicts an acrylamide gel showing intermediate steps and the final result of this process. In Lanes 6 and 7 the upper band corresponds to the 128 bp target ds polynucleotide. This construct was isolated (from a 2% agarose gel; not shown), purified, amplified and both strands Sanger-sequenced. The resulting sequences were identical to the target and to its reverse complement.

Example 3: Post-Processing of Target DNA Sequences for Complex Sequences or RNA Synthesis

3.1 Design of Proxy ds Polynucleotide

In this example a ds polynucleotide was synthesized whose workflow would normally include an ambiguous step such as self-complementary oligo dimer (e.g. FIG. 5A). Since such a self-complementary dimer has to be excluded from the workflow to avoid unwanted runaway reactions, a template sequence was devised by replacing the self-complementary elements with different bases, in such a way that the resulting assembly workflow was unambiguous. According to this template, a proxy ds polynucleotide was synthesized.

In FIG. 5A the sequence of interest is depicted. The underlined parts indicate those parts of the sequence capable of self-complementation and self-polymerization. In order to avoid these sequences a template sequence (FIG. 5B) was designed which comprises two base pair modifications that span three oligos.

The proxy ds polynucleotide was synthesized with the method presented herein as demonstrated in Example 2. The proxy sequence was chosen to coincide with the oligos O−, and V+ of Example 2, and, consequently, its synthesis proceeded exactly as described above.

Once the proxy ds polynucleotide was synthesized, a ds polynucleotide which has a sequence that is identical to the sequence of interest was produced as follows. The principle of directed mutagenesis was applied, that, upon PCR amplification, replaced the part of the target sequence that was excluded in the synthesized proxy ds polynucleotide with the original target sequence.

After synthesis was completed, and the 128 bp proxy ds polynucleotide was purified, a PCR reaction was prepared. In this reaction mix not only the 3' end primers but also a pair of "mutagenizing primers" (AttB) were included. These mutagenizing primers had, on either side of the mutagenized element (in this example, the three bases), ten nucleotides that were fully overlapping with the proxy sequences. With these provisions, a standard PCR was performed, to retrieve the ds polynucleotide which has a sequence that is identical to the SOI, (Sambrook and Russell, 2014; Ch. 13) by using, in this example, commercial kits that standardize the reaction conditions and reagents (Taq PCR Kit, New England Biolabs, product nr. E5000S).

3.2 Production of RNAs

RNA molecules with a given target sequence also have to be produced using proxy ds polynucleotides. This was done in two steps. First, the reverse-complement sequence of the RNA sequence of interest (i.e. the DNA sequence) had to be computed. The DNA sequence is the sequence that will be synthesized. Second, a specific promoter sequence was integrated into the template DNA sequence in order to be recognizable by DNA-dependent enzymes that will later transcribe the DNA into the RNA (Rio, 2011). In this example we used a T7 RNA polymerase I system. The necessary steps are:

A. Design of DNA template. For a given RNA sequence of interest, its DNA reverse complement was computed including the T7 RNA pol promoter sequence TAATACGACTCACTATAG (SEQ ID NO: 24) at the 5' end of the reverse complement.

B. Synthesis of proxy ds polynucleotide. The proxy ds DNA polynucleotide was synthesized according to the DNA template of step 3.2.A as described in Example 2 (see also Examples 1 and 3.1). After synthesis of the proxy DNA its ends were modified to generate blunt ends. The ss overhangs were blunted by incubation at 25° C. for 15 min with one unit per µg of DNA of *E. coli* Polymerase I Large Klenow fragment in the presence of 33 uM of each dNTPs and inactivated by adding ETDA 10 mM and heating at 75° C. for 20 min (obtained from New England Biolabs, product nr. M0210; Sambrook and Russell, 2014; Ch. 12). Next, the proxy ds polynucleotide was purified and, amplified and purified again: a minimum amount of 1 µg DNA is required for the RNA synthesis reaction described below.

C. Transcription, post-processing and purification of RNA. Standard protocols for RNA transcription were followed (for example, the HiScribe T7 ARCA mRNA Kit, New England Biolabs, product nr. E2060, amongst several others) which included the synthesis of the RNA from the proxy DNA. For synthesis of the RNA from the proxy DNA the following protocol was applied:

1-3 ug of DNA were dissolved in a solution composed of 2 µL of 2× rNTP Mix, 2 µL of T7 RNA Polymerase Mix and 18 uL of Nuclease Free Water, followed by incubating at 37° C. for 30 min, thereby producing the RNA molecules. The reaction was stopped by adding 2 µL of DNAse and incubating 15 min at 37° C. to digest the template DNA and then the resulting RNA was purified using spin columns as described in previous examples.

Example 4: Synthesis of a Target DNA Molecule of 608 bp

In this example it is demonstrated how to synthesize a target ds polynucleotide of 608 bp (SOI is Sequence "Ribbon_test_608", SEQ ID NO:26) using the method provided herein. The oligos were part of the library generated in example 1. Oligos had the same properties as in example 2.

The oligos were prepared in an asymmetric way in the reaction plate in order to obtain partial constructs of different sizes at the fourth ligation. The 608 bp sequence is achieved by completing four ligation rounds to obtain one reaction product of 128 bp, and three of 160 bp, which will then were purified and subject to two more ligation rounds, thereby obtaining each strand of the 608 bp target ds polynucleotide.

4.1 Preparing Annealing Solutions

A master mix of 864 µL of annealing solution was prepared, constituted by 772 µL of ddH20 and 92 µL of T4 ligase buffer. 21.6 µL of this solution mix were dispensed into to 38 micro-wells. 0.7 µL of each oligo (in 150 µM) was transferred to a predefined micro-well of the plate and mixed by pipetting.

Partially complementary ss oligos were derived from the library of Example 1 and placed in specific wells on a 96-well plate as indicated in FIG. 6. For simplicity, the oligos were named according to the position on the plate where they are placed for annealing. As in example 2, the leading and lagging strand are denoted by + and − superscripts respectively; see sequences with SEQ ID NO:27 to 102 in FASTA format. Note that wells in rows E-G, columns 2-7 remained empty on purpose.

4.2 Annealing

Annealing was conducted as in example 2.

4.3 Preparing the Ligation Solution

The ligation solution was prepared similarly as in example 2 but adjusting the quantities for 80 µL, enough for 38 reactions wells. Namely: 7.2 µL of Nuclease free ddH2O, 8 µL of Ligase buffer, 40 µL of ATP and after vortex mixing, 24.8 µL of T4 ligase, mixed by pipetting.

2 μL of the resulting solution were transferred with a dispenser to each of the 38 reaction wells in B to prepare them for ligation, followed by gentle mixing by using a multichannel pipette.

4.4 First Four Ligation Rounds

For the first round of ligation the complete contents were transferred from wells in rows A and C into rows B and D of columns (1-7) respectively, and from wells E1 and G1 into F1 and H1, respectively. Transfers were done with a multi-channel pipette, followed by gentle mixing. This scheme is equivalent as in example 2: leftmost contents are transferred to rightmost wells. The plate was sealed and the reaction mix was incubated for at least one hour at 16° C. in a thermocycler. Note that wells E to G from rows 2-7 remained empty.

For the second round of ligation the plate was opened and the complete contents were transferred by pipetting from wells in rows B into row D of columns (1-7), and from well F1 into H1 and mixed. The plate was sealed again and incubated for at least one hour at 16° C.

For the third round of ligation the plate was opened and the complete contents were transferred by pipetting from wells in row D into row H of columns 1-7 by pipetting followed by mixing. The plate was sealed again and incubated for at least one hour at 16° C.

For the fourth round of ligation the plate was opened and the complete contents were transferred by pipetting from wells H2, H4 and H6 into wells H3, H5 and H7, respectively, followed by mixing. Note that well H1 was left untouched. The plate was sealed again and incubated for at least one hour at 16° C.

4.5 Interim Purification

Three agarose gels were prepared as in example 2, part E, with a comb of 7 lanes, including the 50 bp ladder. The contents in well H1 from part D was distributed into six lanes of a gel (33 μL on each lane). The contents H3, H5 and H7 were distributed into three lanes each of the other two gel (41 μL on each lane). Gels were ran as indicated in example 2, part E, followed by bands excision as required (128 for the lanes 2-4 of gel 1, and 80 bp for the remaining lanes of gel 1 and of gel 2). Purification was performed as described in example 2, part E, pooling in the same purification column samples containing the same synthons. Each of the 4 samples was eluted with 10 μL of ddH20 (as indicated in the Zymoclean purification kit), warmed at 35° C. to improve elution efficiency. The contents were transferred to a stripe of PCR reaction tubes and labeled from S1 to S4.

A sample of 0.5 μL form S1 and from S4 was taken and diluted in 0.5 μL of ddH20. These samples were used to estimate the DNA concentration through specrophotometry at 260 nm (nanodrop 2000, Thermo Fisher Scientific), to give 1.52 μg/μL and 1.98 μg/μL respectively. It was assumed that samples S2 and S3 were on a similar range of molar concentrations.

4.6 Preparing the Ligation Solution

Samples were placed in ice. To the samples S1 and S4 0.5 μL of ddH20 were added (to compensate the 0.5 μL taken for measurements in part E). Ligations reactions were prepared by adding to each sample 1.14 μL of ligase buffer. 0.3 μL of T4 ligase were added do S1 and S3. Solutions were mixed by pipetting.

4.7 Last Two Rounds of Ligation

For the fifth ligation reaction the complete contents were transferred by pipetting from tubes 1 and 3 into tubes 2 and 4, respectively, followed by mixing. The tubes were closed. The reactions were incubated in a thermocycler at 16° C. for 80 min.

For the last round of ligation reaction the complete contents were transferred by pipetting from tube 2 into tubes 4, followed by mixing. The tubes were closed. The reactions were incubated in a thermocycler at 16° C. for 80 min. This completed the hierarchical synthesis process.

4.8 Final Purification

Purification was performed from 2% agarose gel using a comb of 8 lanes. First lane contained 50 bp ladder as in example 2 part E. The complete sample was mixed with 10 μL of purple loading die without SDS and dispensed into a single lane. Gel was run at 100 V, 200 mA, 12 watt for 45 min. FIG. 7 shows the resulting gel. The upper band, corresponding to the expected size of 608 bp was excised and purified with Zymo gel extraction kit as in example 2, part E, using 20 μL of ddH20 water warmed to 35° C. Using 0.5 μL if this sample it was estimated spectrophotometrically that the solution contained 10 ng/μL.

4.9 Sequencing

The solution was split into two samples, one of 10 about μL and one of 9.5 μL. To each, a primer ("Primer1" and "Primer2") was added to the solution and sequenced with Sanger methods. Sequencing results in the central reliable region confirmed perfect sequence identity of the target ds polynucleotide with the SOI.

Example 5: Synthesis of a DNA Molecule of 10.000 bp

In this example construction of a ds polynucleotide consisting of a sequence of interest of 10.000 bps is demonstrated based on the library design of Example 1 by using oligos of 26 bps that form ds dimers with 4 nucleotide overhangs.

5.1. Sequence Processing

A. The reverse complement of the leading strand of the sequence of interest is computed, and in both sequences (leading strand and reverse compliment) the last 4 nucleotides at the 3' ends are removed. This results in two single stranded template sequences, one corresponding to the leading strand of the SOI and the other to the reverse complement of the SOI, minus 4 nucleotides at the 3' ends.

B. The sequences of both ss templates are aligned, resulting in a double stranded template sequence, which is then partitioned into shorter sequences, referred to as oligo subsets or sub-sequences, occurring in the oligos contained in the library and their positions in the library are digitally annotated.

C. A workflow is determined which allows unambiguous assembly of the sub-sequences determined in step B.

5.2. Reaction

All steps below, unless otherwise stated, are carried out at 16° C. and all solutions are prepared, and kept, on ice.

A. 700 μL of a solution of 2× ligase buffer in ddH$_2$O is prepared and 1.8 μL of this master mix solution is dispensed in each well of a 384 microwell-plate B. 0.1 μL of each of the oligonucleotide library members corresponding to sub-sequences determined in 4.1, step B of the ss template sequence which is the leading strand of the SOI minus 4 nucleotides at the 3' end, is extracted from the library in order of occurrence in the target sequence and dispensed in a micro-well of the 348 microwell plates, starting at well A1, B1, . . . , P1 and then proceeding to the subsequent column A2, B2, etc. until all oligos are dispensed into a well C. 0.1 μL of each of the oligonucleotide library members corresponding to the sub-sequences determined in 4.1, step B of the ss template sequence which is the reverse complement of the SOI minus 4 nucleotides at the 3' end, is extracted in reverse sequence order and dispensed to the micro-well plate of step B, starting again at well A1 until all oligos are dispensed into a well. At this point, each micro-well contains two oligos that have 22 complementary bps and overhangs comprised of 4 nucleotides. Taken together, the wells should now contain matching pairs of oligonucleotide library members D. The micro-well plate is sealed and annealed in a thermocycler starting at 95° C. and decreased to 16° C. at ramp rate of 1° C. per min E. 800 µL of a master mix ligation reaction solution comprising T4 ligase, at a concentration of 20 cohesive units per µL in ddH20 is prepared and 2 µL of this solution are dispensed into each of the 384 wells of the plate F. The plate is spun down in a centrifuge by a 1000 g pulse G. The rows that contain solution are enumerated using the following formula: $2^{t-1}k$ where t is the tier number and t=1, 2, 3, 4, and k is the index of the rows with filled wells, r=k=1, . . . , $16/2^{t-1}$. In this way, in the first tier all rows are enumerated, in the second tier only half, and so on H. The contents of the wells of each row of odd index are transferred to the wells of the rightmost columns of even index, using a multi-channel micropipette or a liquid handler I. Right after transferring the contents, the solutions are gently mixed by pipetting directly with the micropipette or handler J. The reaction is incubated for 60 min allowing the ligation reaction to complete K. Steps G-J are repeated four more times, until only the last row (P) of the micro-well plate is filled, resulting in a total of 24 remaining filled wells L. The contents of each of the 24 wells (containing 48 µL) are transferred to 24 reaction tubes and prepared for purification in columns following the Monarch PCR & DNA clean up kit from New England Biolabs (product nr. T1030), resulting in 6 µL of purified solution that contain only intermediate reaction products longer than 100 bps M. The purified solutions are transferred to three fresh strips of 8 PCR tubes and arranged in a 8 row×3 column fashion N. 17.5 µL of the solution in step E are taken and 7.5 µL of Ligase buffer (10×) is added for a final concentration of 7×, and 1 µL of this solution is dispensed on each tube O. The reactions proceed in the same way as in steps H-J 3 more times, resulting in three filled tubes (one on each column of the last row)

P. The contents of column 1 are transferred to column 2, leaving column 3 untouched Q. The reaction is incubated for 1 hour R. The contents of column 2 are transferred to column 3

S. The reaction is incubated for 1 hour

T. A 0.8% agarose gel is prepared and the sample loaded together with a 10 kbp ladder. The gel is run at 100 V for 45 minutes U. The band corresponding to 10K bp is extracted and purified from the gel block using standard protocols and kits (Zymo clean is recommended in this example, see also Example 1)

5.3. Finalization and Amplification

A. Two 26 bp long oligos from the library are selected, which are complementary to the last 26 nucleotides at the 3' ends of the SOI, i.e. they also include the 4 nucleotides that were deleted in step A of point 4.1. These two oligos are used as primers in a PCR reaction which is prepared to amplify the final product and to add the remaining 4 bps to each strand to complete the 10.000 bp sequence with blunt ends B. The PCR product is purified with standard kits as in step L of point 4.2 to eliminate remaining oligos, enzymes and reagents, leaving the final DNA product, i.e. the ds polynucleotide which has a sequence that is identical to the SOI, ready for downstream applications.

REFERENCES

Anderson, S., Bankier, A. T., Barrell, B. G. et al. (1981) Sequence and organization of the human mitochondrial genome. *Nature,* 290:457-465.

Beaucage, S. L. and Caruthers, M. H. (1981) Deoxynucleoside phosphoramidites—a new class of key intermediates for deoxypolynucleotide synthesis. *Tetrahedron Letters* 22:1859-1862.

Bentley, D. R., et al. (65 authors) (2008) Accurate Whole Human Genome Sequencing using Reversible Terminator Chemistry. *Nature,* 456:53-59.

Bonde, M. T., Kosuri, S., Genee, H. J., Sarup-Lytzen, K., Church, G. M., Sommer, M. O. A. and Wang H. H. (2014) Direct Mutagenesis of Thousands of Genomic Targets Using Microarray-Derived Oligonucleotides. *ACS Synthetic Biology* 4(1):17-22.

Chari, R. and Church, G. M. (2017) Beyond editing to writing large genomes. *Nature Reviews Genetics,* In Press.

Engler, C., Kandzia, R. and Marillonnet, S. (2008) A one pot, one step, precision cloning method with high through put capability. *PloS One* 3(11):e3647.

Farzadfard, F. and Timothy, K. L. (2014) Genomically Encoded Analog Memory with Precise in Vivo DNA Writing in Living Cell Populations. *Science* 346(6211): 1256272.

Gao, X., LeProust, E. M., Zhang, H., Srivannavit, O. Gulari, E., Yu, P., Nishiguchi, C., Xiang, Q. and Zhou, X. (2001) A Flexible Light-Directed DNA Chip Synthesis Gated by Deprotection Using Solution Photogenerated Acids. *Nucleic Acids Research* 29(22):4744-50.

Gibson, D. G., Young, L., Chuang, R. Y., Venter, J. C., Hutchison III, C. A. and Smith, H. O. (2009) Enzymatic assembly of DNA molecules up to several hundred kilobases. *Nature Methods,* 6(5):343-345.

Horspool, D. R., Coope, R. J. N. and Holt, R. A. (2010) Efficient assembly of very short oligonucleotides using T4 DNA Ligase. *BMC Research Notes,* 3:291-299.

Kai, J., Puntambekar A., Santiago N., Lee S. H., Sehy D. W., Moore V., Han J. and Ahn C. H. (2012) A novel microfluidic microplate as the next generation assay platform for enzyme linked immunoassays (ELISA). *Lab Chip,* 12(21):4257-62

Kemp, G. (1998) Capillary electrophoresis: a versatile family of analytical techniques. *Biotechnology and Applied Biochemistry* 27:9-17.

Lehman, I. R. and Nussbaum, A. L. (1964) The deoxyribonucleases of *Escherichia coli.* V. On the specificity of exonuclease I (phosphodiesterase), *Journal of Biological Chemistry,* 239:2628-2636.

LeProust, E. M., Peck, B. J., Spirin, K., McCuen, H. B., Moore, B., Namsaraev, E., and Caruthers, M. H. (2010) Synthesis of high-quality libraries of long (150 mer) oligonucleotides by a novel depurination controlled process. *Nucleic Acids Research,* 38(8), 2522-2540.

Neuner, P., Cortese, R. and Monaci, P. (1998) Codon-Based Mutagenesis Using Dimer-Phosphoramidites. *Nucleic Acids Research* 26(5):1223-27.

Rio, D. C. (2011). RNA: A Laboratory Manual. New York: Cold Spring Harbor Laboratory Press.

Sambrook, J., and Russell, D. W. (2014). Molecular Cloning. A Laboratory Manual. (3rd ed.). New York: Cold Spring Harbor Laboratory Press.

Smith H. O., Hutchison III, C. A., Pfannkoch, C. and Venter J. C. (2003) Generating a synthetic genome by whole genome assembly: X174 bacteriophage from synthetic oligonucleotides. *Proceedings of the Natural Academy of Sciences of the USA*, 100(26):15440-15445.

Sondek, J., and Shortle, D. (1992). A General Strategy for Random Insertion and Substitution Mutagenesis: Substoichiometric Coupling of Trinucleotide Phosphoramidites. *Proceedings of the National Academy of Sciences* 89(8): 3581-85.

Stemmer, W. P., Crameri, A., Ha, K. D., Brennan, T. M. and Heyneker, H. L. (1995) Single-step assembly of a gene and entire plasmid from large numbers of oligodeoxyribonucleotides. *Gene*, 1614:49-53.

The invention claimed is:

1. A method for synthesizing a target double stranded (ds) polynucleotide having a predefined sequence, comprising:
   a) providing an oligonucleotide library within an array device which comprises a diversity of oligonucleotide library members, wherein each of the library members has a different nucleotide sequence and is contained in a separate library containment in an aqueous solution, wherein the oligonucleotide library members include single stranded oligonucleotides (ss oligos) and double stranded oligonucleotides (ds oligos) with at least one overhang and comprise at least 10,000 pairs of matching oligonucleotides in a separate library containment, wherein said ss oligos each have a length of 6 to 22 nucleotides and said ds oligos each have a length of 6 to 22 base pairs;
   b) in a first assembly step, transferring a first pair of matching oligonucleotides from said library into a first reaction containment using a liquid handler and assembling the matching oligonucleotides, thereby obtaining a first reaction product in said first reaction containment, which first reaction product comprises at least one overhang,
   c) in a second and further assembly steps, transferring a second and further pairs of matching oligonucleotides from said library into separate second and further reaction containments, respectively, using a liquid handler and assembling the matching oligonucleotides, thereby obtaining a second and further reaction products in respective separate second and further reaction compartments, each of said second and further reaction products comprising at least one overhang, wherein each of said pairs of matching oligonucleotides used in steps b) and c) is determined using an algorithm and is assembled in a separate reaction containment, and
   d) assembling said first, second and further reaction products in a predetermined hierarchical workflow, thereby producing said target ds polynucleotide with an overhang, optionally followed by a finalization step to prepare blunt ends.

2. The method of claim 1, wherein a series of different target ds polynucleotides are synthesized using the same oligonucleotide library.

3. The method of claim 2, wherein said different target ds polynucleotides have a sequence identity of less than 50%.

4. The method of claim 1, wherein said overhang is not more than half of the respective ds oligo length.

5. The method of claim 1, wherein the oligonucleotide library members comprise ss oligos and/or ds oligos which are modified by a process selected from the group consisting of any one or more of phosphorylation, methylation, biotinylation, and linkage to a fluorophore or quencher.

6. The method of claim 1, wherein said target ds polynucleotide has a length of at least 48 base pairs.

7. The method of claim 1, wherein said assembly steps comprise a ligation reaction which is an enzymatic and/or chemical reaction.

8. The method of claim 7, wherein said ligation reaction is an enzymatic ligation reaction using a ligase, a polymerase, or a ribozyme.

9. The method of claim 1, wherein said assembly steps are accomplished directly by hybridizing matching overhangs, or indirectly by hybridizing a suitable ss oligo linker, wherein the ss oligo linker is an ss oligo contained in said library which is selected and transferred from said library to assemble any of said first, second or further reaction products.

10. The method of claim 1, wherein the nucleotide sequence of said target ds polynucleotide is identical to a template.

11. The method claim 1, wherein said target ds polynucleotide is further modified by a process selected from the group consisting of any of directed mutagenesis, an endonuclease reaction, and an exonuclease reaction to obtain said polynucleotide which has a sequence of interest (SOI).

12. The method of claim 1, wherein said target ds polynucleotide is further modified to produce a derivative thereof, and wherein the derivative is any one of a ds DNA, ss DNA or RNA molecule.

13. The method of claim 1, wherein said separate library containments are spatially arranged in a three-dimensional order, and wherein said three-dimensional order comprises at least two library containments which are at least partially stacked.

14. The method of claim 1, wherein said array device is any of a microtiter plate, microfluidic microplate, a set of capillaries, a microarray, or a biochip.

15. The method of claim 1, wherein said target ds polynucleotide is sequenced to verify the degree of identity with the sequence of a template or a SOI.

16. An oligonucleotide library provided within an array device comprising a diversity of library members, wherein the library members are single stranded oligonucleotides (ss oligos) and double stranded oligonucleotides (ds oligos) with at least one overhang, wherein each of the library members has a different nucleotide sequence and is contained in a separate library containment in an aqueous solution, the containments being spatially arranged in a three-dimensional order, wherein the library members comprise at least 10,000 pairs of matching oligonucleotides, and wherein said ss oligos have a length of 6 to 22 nucleotides and said ds oligos have a length of 6 to 22 base pairs.

17. The oligonucleotide library of claim 16, wherein said library containments are spatially arranged in a three-dimensional order, and wherein said three-dimensional order comprises at least two library containments which are at least partially stacked.

18. The method of claim 8, wherein the ligase is T3, T4 or T7 DNA ligase.

19. The method of claim 12, wherein said target ds polynucleotide is further modified by an enzymatic modification using a molecule selected from the group consisting of a methyltransferase, a kinase, CRISPR/Cas9, an Argonaute protein (Ago) or a derivative thereof, a zinc-finger nuclease (ZFN), a transcription activator-like effector nuclease (TALEN), a sulfurylase, a recombinase, a nuclease, a DNA polymerase, an RNA polymerase and a TNase.

20. The method of claim 1, wherein the first, second and further assembly steps are carried out in parallel.

21. The method of claim 12, wherein the derivative is a ds DNA, single stranded DNA or RNA molecule comprising the target ds polynucleotide or comprising a polynucleotide comprising at least 90% sequence identity to the target ds polynucleotide.

* * * * *

SEQUENCE LISTING

```
<160> NUMBER OF SEQ ID NOS: 104

<210> SEQ ID NO 1
<211> LENGTH: 128
<212> TYPE: DNA
<213> ORGANISM: Artificial Sequence
<220> FEATURE:
<223> OTHER INFORMATION: Polynucleotide

<400> SEQUENCE: 1
tttcttcttt cgagtttcta tatccgtcgc tggtctgaac ggaaaaatca tcgcacaatc      60
tatgcctacc gttggctgct catgcgtcct tccgacaatc ccatgttcgt ctcgcatccg     120
tttcctgc                                                             128

<210> SEQ ID NO 2
<211> LENGTH: 16
<212> TYPE: DNA
<213> ORGANISM: Artificial Sequence
<220> FEATURE:
<223> OTHER INFORMATION: Oligonucleotide

<400> SEQUENCE: 2
tttcttcttt cgagtt                                                     16

<210> SEQ ID NO 3
<211> LENGTH: 16
<212> TYPE: DNA
<213> ORGANISM: Artificial Sequence
<220> FEATURE:
<223> OTHER INFORMATION: Oligonucleotide

<400> SEQUENCE: 3
tagaaactcg aaagaa                                                     16

<210> SEQ ID NO 4
<211> LENGTH: 16
<212> TYPE: DNA
<213> ORGANISM: Artificial Sequence
<220> FEATURE:
<223> OTHER INFORMATION: Oligonucleotide

<400> SEQUENCE: 4
tctatatccg tcgctg                                                     16

<210> SEQ ID NO 5
<211> LENGTH: 16
<212> TYPE: DNA
<213> ORGANISM: Artificial Sequence
<220> FEATURE:
<223> OTHER INFORMATION: Oligonucleotide

<400> SEQUENCE: 5
agaccagcga cggata                                                     16
```

```
<210> SEQ ID NO 6
<211> LENGTH: 16
<212> TYPE: DNA
<213> ORGANISM: Artificial Sequence
<220> FEATURE:
<223> OTHER INFORMATION: Oligonucleotide

<400> SEQUENCE: 6
gtctgaacgg aaaaat                                                     16

<210> SEQ ID NO 7
<211> LENGTH: 16
<212> TYPE: DNA
<213> ORGANISM: Artificial Sequence
<220> FEATURE:
<223> OTHER INFORMATION: Oligonucleotide

<400> SEQUENCE: 7
gatgattttt ccgttc                                                     16

<210> SEQ ID NO 8
<211> LENGTH: 16
<212> TYPE: DNA
<213> ORGANISM: Artificial Sequence
<220> FEATURE:
<223> OTHER INFORMATION: Oligonucleotide

<400> SEQUENCE: 8
catcgcacaa tctatg                                                     16

<210> SEQ ID NO 9
<211> LENGTH: 16
<212> TYPE: DNA
<213> ORGANISM: Artificial Sequence
<220> FEATURE:
<223> OTHER INFORMATION: Oligonucleotide

<400> SEQUENCE: 9
taggcataga ttgtgc                                                     16

<210> SEQ ID NO 10
<211> LENGTH: 16
<212> TYPE: DNA
<213> ORGANISM: Artificial Sequence
<220> FEATURE:
<223> OTHER INFORMATION: Oligonucleotide

<400> SEQUENCE: 10
cctaccgttg gctgct                                                     16

<210> SEQ ID NO 11
<211> LENGTH: 16
<212> TYPE: DNA
<213> ORGANISM: Artificial Sequence
<220> FEATURE:
<223> OTHER INFORMATION: Oligonucleotide

<400> SEQUENCE: 11
catgagcagc caacgg                                                     16

<210> SEQ ID NO 12
<211> LENGTH: 16
<212> TYPE: DNA
<213> ORGANISM: Artificial Sequence
<220> FEATURE:
<223> OTHER INFORMATION: Oligonucleotide
```

```
<400> SEQUENCE: 12
catgcgtcct tccgac                                                    16

<210> SEQ ID NO 13
<211> LENGTH: 16
<212> TYPE: DNA
<213> ORGANISM: Artificial Sequence
<220> FEATURE:
<223> OTHER INFORMATION: Oligonucleotide

<400> SEQUENCE: 13
gattgtcgga aggacg                                                    16

<210> SEQ ID NO 14
<211> LENGTH: 16
<212> TYPE: DNA
<213> ORGANISM: Artificial Sequence
<220> FEATURE:
<223> OTHER INFORMATION: Oligonucleotide

<400> SEQUENCE: 14
aatcccatgt tcgtct                                                    16

<210> SEQ ID NO 15
<211> LENGTH: 16
<212> TYPE: DNA
<213> ORGANISM: Artificial Sequence
<220> FEATURE:
<223> OTHER INFORMATION: Oligonucleotide

<400> SEQUENCE: 15
tgcgagacga acatgg                                                    16

<210> SEQ ID NO 16
<211> LENGTH: 16
<212> TYPE: DNA
<213> ORGANISM: Artificial Sequence
<220> FEATURE:
<223> OTHER INFORMATION: Oligonucleotide

<400> SEQUENCE: 16
cgcatccgtt tcctgc                                                    16

<210> SEQ ID NO 17
<211> LENGTH: 16
<212> TYPE: DNA
<213> ORGANISM: Artificial Sequence
<220> FEATURE:
<223> OTHER INFORMATION: Oligonucleotide

<400> SEQUENCE: 17
gcgtgcagga aacgga                                                    16

<210> SEQ ID NO 18
<211> LENGTH: 36
<212> TYPE: DNA
<213> ORGANISM: Artificial Sequence
<220> FEATURE:
<223> OTHER INFORMATION: Polynucleotide

<400> SEQUENCE: 18
cctaccgttg gctgctaatc cgtccttccg acaatc                              36

<210> SEQ ID NO 19
```

```
<211> LENGTH: 32
<212> TYPE: DNA
<213> ORGANISM: Artificial Sequence
<220> FEATURE:
<223> OTHER INFORMATION: Polynucleotide

<400> SEQUENCE: 19
ggcaaccgac gattaggcag gaaggctgtt ag                              32

<210> SEQ ID NO 20
<211> LENGTH: 36
<212> TYPE: DNA
<213> ORGANISM: Artificial Sequence
<220> FEATURE:
<223> OTHER INFORMATION: Polynucleotide

<400> SEQUENCE: 20
cctaccgttg gctgctcatg cgtccttccg acaatc                          36

<210> SEQ ID NO 21
<211> LENGTH: 32
<212> TYPE: DNA
<213> ORGANISM: Artificial Sequence
<220> FEATURE:
<223> OTHER INFORMATION: Polynucleotide

<400> SEQUENCE: 21
ggcaaccgac gagtacgcag gaaggctgtt ag                              32

<210> SEQ ID NO 22
<211> LENGTH: 24
<212> TYPE: DNA
<213> ORGANISM: Artificial Sequence
<220> FEATURE:
<223> OTHER INFORMATION: Polynucleotide

<400> SEQUENCE: 22
gttggctgct aatccgtcct tccg                                       24

<210> SEQ ID NO 23
<211> LENGTH: 24
<212> TYPE: DNA
<213> ORGANISM: Artificial Sequence
<220> FEATURE:
<223> OTHER INFORMATION: Polynucleotide

<400> SEQUENCE: 23
cggaaggacg catgagcagc caac                                       24

<210> SEQ ID NO 24
<211> LENGTH: 18
<212> TYPE: DNA
<213> ORGANISM: Artificial Sequence
<220> FEATURE:
<223> OTHER INFORMATION: Polynucleotide

<400> SEQUENCE: 24
taatacgact cactatag                                              18

<210> SEQ ID NO 25
<211> LENGTH: 16
<212> TYPE: DNA
<213> ORGANISM: Artificial Sequence
<220> FEATURE:
<223> OTHER INFORMATION: Oligonucleotide
```

<400> SEQUENCE: 25
aagaaagctc aaagat                                                      16

<210> SEQ ID NO 26
<211> LENGTH: 608
<212> TYPE: DNA
<213> ORGANISM: Artificial Sequence
<220> FEATURE:
<223> OTHER INFORMATION: Polynucleotide

<400> SEQUENCE: 26
tttcttcttt cgagtttcta tatccgtcgc tggtctgaac ggaaaaatca tcgcacaatc      60
tatgcctacc gttggctgct catgcgtcct tccgacaatc ccatgttcgt ctcgcatccg     120
tttcctgcac gcaccccccc ctgtactttg gaaagcggcc atcttaacac tctcccaact     180
ttttaaatgc gtcgaagccc tgggcatctg gtttccacta gcctagtcgg gtgttggata     240
cgccgagagt tatggtgtag ctgtgtgcgc gaaccgacgg gtggaaattg ctgaccgatt     300
ttcaaatagt tctcaggaag ccgatggcag ttacggcttg cgactcgggg caccgtgagc     360
ctcttctccc tctagaagtc gaagcaaggg acactatcct aaatgccatg gactagcgcg     420
cgcgaaatcg atgcactcct tattaatgtg atctgcgcaa gttgttcagc catcggtcat     480
tttgcgttga tattcggttc tttgatttgc gtgccatgct ataacagga cacttattgt      540
gccccagctc ttctcatgca agtgcggttt tctctagcta ctgtggtgtg cgctcatcaa     600
tactccag                                                              608

<210> SEQ ID NO 27
<211> LENGTH: 16
<212> TYPE: DNA
<213> ORGANISM: Artificial Sequence
<220> FEATURE:
<223> OTHER INFORMATION: Oligonucleotide

<400> SEQUENCE: 27
tttcttcttt cgagtt                                                      16

<210> SEQ ID NO 28
<211> LENGTH: 16
<212> TYPE: DNA
<213> ORGANISM: Artificial Sequence
<220> FEATURE:
<223> OTHER INFORMATION: Oligonucleotide

<400> SEQUENCE: 28
tagaaactcg aaagaa                                                      16

<210> SEQ ID NO 29
<211> LENGTH: 16
<212> TYPE: DNA
<213> ORGANISM: Artificial Sequence
<220> FEATURE:
<223> OTHER INFORMATION: Oligonucleotide

<400> SEQUENCE: 29
tctatatccg tcgctg                                                      16

<210> SEQ ID NO 30
<211> LENGTH: 16
<212> TYPE: DNA
<213> ORGANISM: Artificial Sequence
<220> FEATURE:

<223> OTHER INFORMATION: Oligonucleotide

<400> SEQUENCE: 30
agaccagcga cggata                                                         16

<210> SEQ ID NO 31
<211> LENGTH: 16
<212> TYPE: DNA
<213> ORGANISM: Artificial Sequence
<220> FEATURE:
<223> OTHER INFORMATION: Oligonucleotide

<400> SEQUENCE: 31
gtctgaacgg aaaaat                                                         16

<210> SEQ ID NO 32
<211> LENGTH: 16
<212> TYPE: DNA
<213> ORGANISM: Artificial Sequence
<220> FEATURE:
<223> OTHER INFORMATION: Oligonucleotide

<400> SEQUENCE: 32
gatgattttt ccgttc                                                         16

<210> SEQ ID NO 33
<211> LENGTH: 16
<212> TYPE: DNA
<213> ORGANISM: Artificial Sequence
<220> FEATURE:
<223> OTHER INFORMATION: Oligonucleotide

<400> SEQUENCE: 33
catcgcacaa tctatg                                                         16

<210> SEQ ID NO 34
<211> LENGTH: 16
<212> TYPE: DNA
<213> ORGANISM: Artificial Sequence
<220> FEATURE:
<223> OTHER INFORMATION: Oligonucleotide

<400> SEQUENCE: 34
taggcataga ttgtgc                                                         16

<210> SEQ ID NO 35
<211> LENGTH: 16
<212> TYPE: DNA
<213> ORGANISM: Artificial Sequence
<220> FEATURE:
<223> OTHER INFORMATION: Oligonucleotide

<400> SEQUENCE: 35
cctaccgttg gctgct                                                         16

<210> SEQ ID NO 36
<211> LENGTH: 16
<212> TYPE: DNA
<213> ORGANISM: Artificial Sequence
<220> FEATURE:
<223> OTHER INFORMATION: Oligonucleotide

<400> SEQUENCE: 36
catgagcagc caacgg                                                         16

```
<210> SEQ ID NO 37
<211> LENGTH: 16
<212> TYPE: DNA
<213> ORGANISM: Artificial Sequence
<220> FEATURE:
<223> OTHER INFORMATION: Oligonucleotide

<400> SEQUENCE: 37
catgcgtcct tccgac                                                  16

<210> SEQ ID NO 38
<211> LENGTH: 16
<212> TYPE: DNA
<213> ORGANISM: Artificial Sequence
<220> FEATURE:
<223> OTHER INFORMATION: Oligonucleotide

<400> SEQUENCE: 38
gattgtcgga aggacg                                                  16

<210> SEQ ID NO 39
<211> LENGTH: 16
<212> TYPE: DNA
<213> ORGANISM: Artificial Sequence
<220> FEATURE:
<223> OTHER INFORMATION: Oligonucleotide

<400> SEQUENCE: 39
aatcccatgt tcgtct                                                  16

<210> SEQ ID NO 40
<211> LENGTH: 16
<212> TYPE: DNA
<213> ORGANISM: Artificial Sequence
<220> FEATURE:
<223> OTHER INFORMATION: Oligonucleotide

<400> SEQUENCE: 40
tgcgagacga acatgg                                                  16

<210> SEQ ID NO 41
<211> LENGTH: 16
<212> TYPE: DNA
<213> ORGANISM: Artificial Sequence
<220> FEATURE:
<223> OTHER INFORMATION: Oligonucleotide

<400> SEQUENCE: 41
cgcatccgtt tcctgc                                                  16

<210> SEQ ID NO 42
<211> LENGTH: 16
<212> TYPE: DNA
<213> ORGANISM: Artificial Sequence
<220> FEATURE:
<223> OTHER INFORMATION: Oligonucleotide

<400> SEQUENCE: 42
gcgtgcagga aacgga                                                  16

<210> SEQ ID NO 43
<211> LENGTH: 16
<212> TYPE: DNA
<213> ORGANISM: Artificial Sequence
<220> FEATURE:
<223> OTHER INFORMATION: Oligonucleotide
```

```
<400> SEQUENCE: 43
acgcaccccc ccctgt                                                     16

<210> SEQ ID NO 44
<211> LENGTH: 16
<212> TYPE: DNA
<213> ORGANISM: Artificial Sequence
<220> FEATURE:
<223> OTHER INFORMATION: Oligonucleotide

<400> SEQUENCE: 44
aagtacaggg gggggt                                                     16

<210> SEQ ID NO 45
<211> LENGTH: 16
<212> TYPE: DNA
<213> ORGANISM: Artificial Sequence
<220> FEATURE:
<223> OTHER INFORMATION: Oligonucleotide

<400> SEQUENCE: 45
actttggaaa gcggcc                                                     16

<210> SEQ ID NO 46
<211> LENGTH: 16
<212> TYPE: DNA
<213> ORGANISM: Artificial Sequence
<220> FEATURE:
<223> OTHER INFORMATION: Oligonucleotide

<400> SEQUENCE: 46
agatggccgc tttcca                                                     16

<210> SEQ ID NO 47
<211> LENGTH: 16
<212> TYPE: DNA
<213> ORGANISM: Artificial Sequence
<220> FEATURE:
<223> OTHER INFORMATION: Oligonucleotide

<400> SEQUENCE: 47
atcttaacac tctccc                                                     16

<210> SEQ ID NO 48
<211> LENGTH: 16
<212> TYPE: DNA
<213> ORGANISM: Artificial Sequence
<220> FEATURE:
<223> OTHER INFORMATION: Oligonucleotide

<400> SEQUENCE: 48
agttgggaga gtgtta                                                     16

<210> SEQ ID NO 49
<211> LENGTH: 16
<212> TYPE: DNA
<213> ORGANISM: Artificial Sequence
<220> FEATURE:
<223> OTHER INFORMATION: Oligonucleotide

<400> SEQUENCE: 49 aacttttta atgcgt                                                      16

<210> SEQ ID NO 50
<211> LENGTH: 16
```

<212> TYPE: DNA
<213> ORGANISM: Artificial Sequence
<220> FEATURE:
<223> OTHER INFORMATION: Oligonucleotide

<400> SEQUENCE: 50
ttcgacgcat ttaaaa                                                     16

<210> SEQ ID NO 51
<211> LENGTH: 16
<212> TYPE: DNA
<213> ORGANISM: Artificial Sequence
<220> FEATURE:
<223> OTHER INFORMATION: Oligonucleotide

<400> SEQUENCE: 51
cgaagccctg ggcatc                                                     16

<210> SEQ ID NO 52
<211> LENGTH: 16
<212> TYPE: DNA
<213> ORGANISM: Artificial Sequence
<220> FEATURE:
<223> OTHER INFORMATION: Oligonucleotide

<400> SEQUENCE: 52
accagatgcc cagggc                                                     16

<210> SEQ ID NO 53
<211> LENGTH: 16
<212> TYPE: DNA
<213> ORGANISM: Artificial Sequence
<220> FEATURE:
<223> OTHER INFORMATION: Oligonucleotide

<400> SEQUENCE: 53
tggtttccac tagcct                                                     16

<210> SEQ ID NO 54
<211> LENGTH: 16
<212> TYPE: DNA
<213> ORGANISM: Artificial Sequence
<220> FEATURE:
<223> OTHER INFORMATION: Oligonucleotide

<400> SEQUENCE: 54
gactaggcta gtggaa                                                     16

<210> SEQ ID NO 55
<211> LENGTH: 16
<212> TYPE: DNA
<213> ORGANISM: Artificial Sequence
<220> FEATURE:
<223> OTHER INFORMATION: Oligonucleotide

<400> SEQUENCE: 55
agtcgggtgt tggata                                                     16

<210> SEQ ID NO 56
<211> LENGTH: 16
<212> TYPE: DNA
<213> ORGANISM: Artificial Sequence
<220> FEATURE:
<223> OTHER INFORMATION: Oligonucleotide

<400> SEQUENCE: 56
ggcgtatcca acaccc                                                      16

<210> SEQ ID NO 57
<211> LENGTH: 16
<212> TYPE: DNA
<213> ORGANISM: Artificial Sequence
<220> FEATURE:
<223> OTHER INFORMATION: Oligonucleotide

<400> SEQUENCE: 57
cgccgagagt tatggt                                                      16

<210> SEQ ID NO 58
<211> LENGTH: 16
<212> TYPE: DNA
<213> ORGANISM: Artificial Sequence
<220> FEATURE:
<223> OTHER INFORMATION: Oligonucleotide

<400> SEQUENCE: 58
ctacaccata actctc                                                      16

<210> SEQ ID NO 59
<211> LENGTH: 16
<212> TYPE: DNA
<213> ORGANISM: Artificial Sequence
<220> FEATURE:
<223> OTHER INFORMATION: Oligonucleotide

<400> SEQUENCE: 59
gtagctgtgt gcgcga                                                      16

<210> SEQ ID NO 60
<211> LENGTH: 16
<212> TYPE: DNA
<213> ORGANISM: Artificial Sequence
<220> FEATURE:
<223> OTHER INFORMATION: Oligonucleotide

<400> SEQUENCE: 60
cggttcgcgc acacag                                                      16

<210> SEQ ID NO 61
<211> LENGTH: 16
<212> TYPE: DNA
<213> ORGANISM: Artificial Sequence
<220> FEATURE:
<223> OTHER INFORMATION: Oligonucleotide

<400> SEQUENCE: 61
accgacgggt ggaaat                                                      16

<210> SEQ ID NO 62
<211> LENGTH: 16
<212> TYPE: DNA
<213> ORGANISM: Artificial Sequence
<220> FEATURE:
<223> OTHER INFORMATION: Oligonucleotide

<400> SEQUENCE: 62
agcaatttcc acccgt                                                      16

<210> SEQ ID NO 63

```
<211> LENGTH: 16
<212> TYPE: DNA
<213> ORGANISM: Artificial Sequence
<220> FEATURE:
<223> OTHER INFORMATION: Oligonucleotide

<400> SEQUENCE: 63
tgctgaccga ttttca                                                       16

<210> SEQ ID NO 64
<211> LENGTH: 16
<212> TYPE: DNA
<213> ORGANISM: Artificial Sequence
<220> FEATURE:
<223> OTHER INFORMATION: Oligonucleotide

<400> SEQUENCE: 64
tatttgaaaa tcggtc                                                       16

<210> SEQ ID NO 65
<211> LENGTH: 16
<212> TYPE: DNA
<213> ORGANISM: Artificial Sequence
<220> FEATURE:
<223> OTHER INFORMATION: Oligonucleotide

<400> SEQUENCE: 65
aatagttctc aggaag                                                       16

<210> SEQ ID NO 66
<211> LENGTH: 16
<212> TYPE: DNA
<213> ORGANISM: Artificial Sequence
<220> FEATURE:
<223> OTHER INFORMATION: Oligonucleotide

<400> SEQUENCE: 66
tcggcttcct gagaac                                                       16

<210> SEQ ID NO 67
<211> LENGTH: 16
<212> TYPE: DNA
<213> ORGANISM: Artificial Sequence
<220> FEATURE:
<223> OTHER INFORMATION: Oligonucleotide

<400> SEQUENCE: 67
ccgatggcag ttacgg                                                       16

<210> SEQ ID NO 68
<211> LENGTH: 16
<212> TYPE: DNA
<213> ORGANISM: Artificial Sequence
<220> FEATURE:
<223> OTHER INFORMATION: Oligonucleotide

<400> SEQUENCE: 68
caagccgtaa ctgcca                                                       16

<210> SEQ ID NO 69
<211> LENGTH: 16
<212> TYPE: DNA
<213> ORGANISM: Artificial Sequence
<220> FEATURE:
<223> OTHER INFORMATION: Oligonucleotide
```

```
<400> SEQUENCE: 69
cttgcgactc ggggca                                                    16

<210> SEQ ID NO 70
<211> LENGTH: 16
<212> TYPE: DNA
<213> ORGANISM: Artificial Sequence
<220> FEATURE:
<223> OTHER INFORMATION: Oligonucleotide

<400> SEQUENCE: 70
acggtgcccc gagtcg                                                    16

<210> SEQ ID NO 71
<211> LENGTH: 16
<212> TYPE: DNA
<213> ORGANISM: Artificial Sequence
<220> FEATURE:
<223> OTHER INFORMATION: Oligonucleotide

<400> SEQUENCE: 71
ccgtgagcct cttctc                                                    16

<210> SEQ ID NO 72
<211> LENGTH: 16
<212> TYPE: DNA
<213> ORGANISM: Artificial Sequence
<220> FEATURE:
<223> OTHER INFORMATION: Oligonucleotide

<400> SEQUENCE: 72
gagggagaag aggctc                                                    16

<210> SEQ ID NO 73
<211> LENGTH: 16
<212> TYPE: DNA
<213> ORGANISM: Artificial Sequence
<220> FEATURE:
<223> OTHER INFORMATION: Oligonucleotide

<400> SEQUENCE: 73
cctctagaag tcgaag                                                    16

<210> SEQ ID NO 74
<211> LENGTH: 16
<212> TYPE: DNA
<213> ORGANISM: Artificial Sequence
<220> FEATURE:
<223> OTHER INFORMATION: Oligonucleotide

<400> SEQUENCE: 74
cttgcttcga cttcta                                                    16

<210> SEQ ID NO 75
<211> LENGTH: 16
<212> TYPE: DNA
<213> ORGANISM: Artificial Sequence
<220> FEATURE:
<223> OTHER INFORMATION: Oligonucleotide

<400> SEQUENCE: 75
caagggacac tatcct                                                    16

<210> SEQ ID NO 76
```

```
<211> LENGTH: 16
<212> TYPE: DNA
<213> ORGANISM: Artificial Sequence
<220> FEATURE:
<223> OTHER INFORMATION: Oligonucleotide

<400> SEQUENCE: 76
atttaggata gtgtcc                                                      16

<210> SEQ ID NO 77
<211> LENGTH: 16
<212> TYPE: DNA
<213> ORGANISM: Artificial Sequence
<220> FEATURE:
<223> OTHER INFORMATION: Oligonucleotide

<400> SEQUENCE: 77
aaatgccatg gactag                                                      16

<210> SEQ ID NO 78
<211> LENGTH: 16
<212> TYPE: DNA
<213> ORGANISM: Artificial Sequence
<220> FEATURE:
<223> OTHER INFORMATION: Oligonucleotide

<400> SEQUENCE: 78
cgcgctagtc catggc                                                      16

<210> SEQ ID NO 79
<211> LENGTH: 16
<212> TYPE: DNA
<213> ORGANISM: Artificial Sequence
<220> FEATURE:
<223> OTHER INFORMATION: Oligonucleotide

<400> SEQUENCE: 79
cgcgcgcgaa atcgat                                                      16

<210> SEQ ID NO 80
<211> LENGTH: 16
<212> TYPE: DNA
<213> ORGANISM: Artificial Sequence
<220> FEATURE:
<223> OTHER INFORMATION: Oligonucleotide

<400> SEQUENCE: 80
gtgcatcgat ttcgcg                                                      16

<210> SEQ ID NO 81
<211> LENGTH: 16
<212> TYPE: DNA
<213> ORGANISM: Artificial Sequence
<220> FEATURE:
<223> OTHER INFORMATION: Oligonucleotide

<400> SEQUENCE: 81
gcactcctta ttaatg                                                      16

<210> SEQ ID NO 82
<211> LENGTH: 16
<212> TYPE: DNA
<213> ORGANISM: Artificial Sequence
<220> FEATURE:
<223> OTHER INFORMATION: Oligonucleotide
```

```
<400> SEQUENCE: 82
atcacattaa taagga                                                      16

<210> SEQ ID NO 83
<211> LENGTH: 16
<212> TYPE: DNA
<213> ORGANISM: Artificial Sequence
<220> FEATURE:
<223> OTHER INFORMATION: Oligonucleotide

<400> SEQUENCE: 83
tgatctgcgc aagttg                                                      16

<210> SEQ ID NO 84
<211> LENGTH: 16
<212> TYPE: DNA
<213> ORGANISM: Artificial Sequence
<220> FEATURE:
<223> OTHER INFORMATION: Oligonucleotide

<400> SEQUENCE: 84
tgaacaactt gcgcag                                                      16

<210> SEQ ID NO 85
<211> LENGTH: 16
<212> TYPE: DNA
<213> ORGANISM: Artificial Sequence
<220> FEATURE:
<223> OTHER INFORMATION: Oligonucleotide

<400> SEQUENCE: 85
ttcagccatc ggtcat                                                      16

<210> SEQ ID NO 86
<211> LENGTH: 16
<212> TYPE: DNA
<213> ORGANISM: Artificial Sequence
<220> FEATURE:
<223> OTHER INFORMATION: Oligonucleotide

<400> SEQUENCE: 86
caaaatgacc gatggc                                                      16

<210> SEQ ID NO 87
<211> LENGTH: 16
<212> TYPE: DNA
<213> ORGANISM: Artificial Sequence
<220> FEATURE:
<223> OTHER INFORMATION: Oligonucleotide

<400> SEQUENCE: 87
tttgcgttga tattcg                                                      16

<210> SEQ ID NO 88
<211> LENGTH: 16
<212> TYPE: DNA
<213> ORGANISM: Artificial Sequence
<220> FEATURE:
<223> OTHER INFORMATION: Oligonucleotide

<400> SEQUENCE: 88
gaaccgaata tcaacg                                                      16

<210> SEQ ID NO 89
```

```
<211> LENGTH: 16
<212> TYPE: DNA
<213> ORGANISM: Artificial Sequence
<220> FEATURE:
<223> OTHER INFORMATION: Oligonucleotide

<400> SEQUENCE: 89
gttctttgat ttgcgt                                                        16

<210> SEQ ID NO 90
<211> LENGTH: 16
<212> TYPE: DNA
<213> ORGANISM: Artificial Sequence
<220> FEATURE:
<223> OTHER INFORMATION: Oligonucleotide

<400> SEQUENCE: 90
tggcacgcaa atcaaa                                                        16

<210> SEQ ID NO 91
<211> LENGTH: 16
<212> TYPE: DNA
<213> ORGANISM: Artificial Sequence
<220> FEATURE:
<223> OTHER INFORMATION: Oligonucleotide

<400> SEQUENCE: 91
gccatgctta taacag                                                        16

<210> SEQ ID NO 92
<211> LENGTH: 16
<212> TYPE: DNA
<213> ORGANISM: Artificial Sequence
<220> FEATURE:
<223> OTHER INFORMATION: Oligonucleotide

<400> SEQUENCE: 92
tgtcctgtta taagca                                                        16

<210> SEQ ID NO 93
<211> LENGTH: 16
<212> TYPE: DNA
<213> ORGANISM: Artificial Sequence
<220> FEATURE:
<223> OTHER INFORMATION: Oligonucleotide

<400> SEQUENCE: 93
gacacttatt gtgccc                                                        16

<210> SEQ ID NO 94
<211> LENGTH: 16
<212> TYPE: DNA
<213> ORGANISM: Artificial Sequence
<220> FEATURE:
<223> OTHER INFORMATION: Oligonucleotide

<400> SEQUENCE: 94
gctggggcac aataag                                                        16

<210> SEQ ID NO 95
<211> LENGTH: 16
<212> TYPE: DNA
<213> ORGANISM: Artificial Sequence
<220> FEATURE:
<223> OTHER INFORMATION: Oligonucleotide
```

<400> SEQUENCE: 95
cagctcttct catgca                                                    16

<210> SEQ ID NO 96
<211> LENGTH: 16
<212> TYPE: DNA
<213> ORGANISM: Artificial Sequence
<220> FEATURE:
<223> OTHER INFORMATION: Oligonucleotide

<400> SEQUENCE: 96
cacttgcatg agaaga                                                    16

<210> SEQ ID NO 97
<211> LENGTH: 16
<212> TYPE: DNA
<213> ORGANISM: Artificial Sequence
<220> FEATURE:
<223> OTHER INFORMATION: Oligonucleotide

<400> SEQUENCE: 97
agtgcggttt tctcta                                                    16

<210> SEQ ID NO 98
<211> LENGTH: 16
<212> TYPE: DNA
<213> ORGANISM: Artificial Sequence
<220> FEATURE:
<223> OTHER INFORMATION: Oligonucleotide

<400> SEQUENCE: 98
tagctagaga aaaccg                                                    16

<210> SEQ ID NO 99
<211> LENGTH: 16
<212> TYPE: DNA
<213> ORGANISM: Artificial Sequence
<220> FEATURE:
<223> OTHER INFORMATION: Oligonucleotide

<400> SEQUENCE: 99
gctactgtgg tgtgcg                                                    16

<210> SEQ ID NO 100
<211> LENGTH: 16
<212> TYPE: DNA
<213> ORGANISM: Artificial Sequence
<220> FEATURE:
<223> OTHER INFORMATION: Oligonucleotide

<400> SEQUENCE: 100
tgagcgcaca ccacag                                                    16

<210> SEQ ID NO 101
<211> LENGTH: 16
<212> TYPE: DNA
<213> ORGANISM: Artificial Sequence
<220> FEATURE:
<223> OTHER INFORMATION: Oligonucleotide

<400> SEQUENCE: 101
ctcatcaata ctccag                                                    16

<210> SEQ ID NO 102

```
<211> LENGTH: 16
<212> TYPE: DNA
<213> ORGANISM: Artificial Sequence
<220> FEATURE:
<223> OTHER INFORMATION: Oligonucleotide

<400> SEQUENCE: 102
ttatctggag tattga                                                         16

<210> SEQ ID NO 103
<211> LENGTH: 32
<212> TYPE: DNA
<213> ORGANISM: Artificial Sequence
<220> FEATURE:
<223> OTHER INFORMATION: Primer

<400> SEQUENCE: 103
tttcttcttt cgagtttcta tatccgtcgc tg                                        32

<210> SEQ ID NO 104
<211> LENGTH: 25
<212> TYPE: DNA
<213> ORGANISM: Artificial Sequence
<220> FEATURE:
<223> OTHER INFORMATION: Primer

<400> SEQUENCE: 104
ttatctggag tattgatgag cgcac                                                25
```